United States Patent
Stahmann et al.

(10) Patent No.: US 10,449,361 B2
(45) Date of Patent: Oct. 22, 2019

(54) SYSTEMS AND METHODS FOR TREATING CARDIAC ARRHYTHMIAS

(71) Applicant: Cardiac Pacemakers, Inc., St. Paul, MN (US)

(72) Inventors: Jeffrey E. Stahmann, Ramsey, MN (US); Howard D. Simms, Jr., Shoreview, MN (US); Keith R. Maile, New Brighton, MN (US); Michael J. Kane, Roseville, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 314 days.

(21) Appl. No.: 14/592,723

(22) Filed: Jan. 8, 2015

(65) Prior Publication Data
US 2015/0196756 A1    Jul. 16, 2015

Related U.S. Application Data

(60) Provisional application No. 61/926,068, filed on Jan. 10, 2014.

(51) Int. Cl.
*A61N 1/362* (2006.01)
*A61N 1/372* (2006.01)
(Continued)

(52) U.S. Cl.
CPC ......... *A61N 1/3621* (2013.01); *A61N 1/3756* (2013.01); *A61N 1/37288* (2013.01); *A61N 1/3962* (2013.01)

(58) Field of Classification Search
CPC .................................................. A61N 1/3962
See application file for complete search history.

(56) References Cited

U.S. PATENT DOCUMENTS

| 4,333,470 A | 6/1982 | Barthel |
| 4,531,527 A | 7/1985 | Reinhold, Jr. et al. |

(Continued)

FOREIGN PATENT DOCUMENTS

| EP | 0253505 A2 | 1/1988 |
| EP | 0308536 A1 | 3/1989 |

(Continued)

OTHER PUBLICATIONS

Duru et al., "The Potential for Inappropriate Ventricular Tachycardia Confirmation Using the Intracardiac Electrogram (EGM) Width Criterion", Pacing and Clinical Electrophysiology [PACE], 22(7): 1039-1046, Jul. 1999.

(Continued)

*Primary Examiner* — Carl H Layno
*Assistant Examiner* — Jennifer L Ghand
(74) *Attorney, Agent, or Firm* — Seager, Tufte & Wickhem LLP.

(57) ABSTRACT

Systems and methods for coordinating treatment of abnormal heart activity using multiple implanted devices within a patient. In one example, abnormal heart activity may be sensed by a medical device system. One of the devices of the system may determine to deliver anti-tachycardia pacing therapy to the heart of the patient, and may communicate an instruction to another of the devices of the medical device system to deliver anti-tachycardia pacing (ATP) therapy to the heart. The receiving medical device may then deliver ATP therapy to the heart of the patient.

15 Claims, 16 Drawing Sheets

(51) Int. Cl.
*A61N 1/375* (2006.01)
*A61N 1/39* (2006.01)

(56) References Cited

U.S. PATENT DOCUMENTS

| | | |
|---|---|---|
| 4,539,999 A | 9/1985 | Mans |
| 4,562,841 A | 1/1986 | Brockway et al. |
| 4,585,004 A | 4/1986 | Brownlee |
| 4,589,420 A | 5/1986 | Adams et al. |
| RE32,378 E | 3/1987 | Barthel |
| 4,787,389 A | 11/1988 | Tarjan |
| 4,884,345 A | 12/1989 | Long |
| 4,924,875 A | 5/1990 | Chamoun |
| 5,000,189 A | 3/1991 | Throne et al. |
| 5,002,052 A | 3/1991 | Haluska |
| 5,014,698 A | 5/1991 | Cohen |
| 5,107,850 A | 4/1992 | Olive |
| 5,113,869 A | 5/1992 | Nappholz et al. |
| 5,117,824 A | 6/1992 | Keimel et al. |
| 5,127,401 A | 7/1992 | Grevoius et al. |
| 5,139,028 A | 8/1992 | Steinhaus et al. |
| 5,156,148 A | 10/1992 | Cohen |
| 5,161,527 A | 11/1992 | Nappholz et al. |
| 5,193,550 A | 3/1993 | Duffin |
| 5,205,283 A | 4/1993 | Olson |
| 5,215,098 A | 6/1993 | Steinhaus et al. |
| 5,217,021 A | 6/1993 | Steinhaus et al. |
| 5,255,186 A | 10/1993 | Steinhaus et al. |
| 5,265,602 A | 11/1993 | Anderson et al. |
| 5,271,411 A | 12/1993 | Ripley et al. |
| 5,273,049 A | 12/1993 | Steinhaus et al. |
| 5,275,621 A | 1/1994 | Mehra |
| 5,292,348 A | 3/1994 | Saumarez et al. |
| 5,312,445 A | 5/1994 | Nappholz et al. |
| 5,313,953 A | 5/1994 | Yomtov et al. |
| 5,324,310 A | 6/1994 | Greeninger et al. |
| 5,331,966 A | 7/1994 | Bennett et al. |
| 5,360,436 A | 11/1994 | Alt et al. |
| 5,366,487 A | 11/1994 | Adams et al. |
| 5,378,775 A | 1/1995 | Shimizu et al. |
| 5,379,775 A | 1/1995 | Kruse |
| 5,379,776 A | 1/1995 | Murphy et al. |
| 5,388,578 A | 2/1995 | Yomtov et al. |
| 5,400,795 A | 3/1995 | Murphy et al. |
| 5,411,031 A | 5/1995 | Yomtov |
| 5,447,524 A | 9/1995 | Alt |
| 5,448,997 A | 9/1995 | Kruse et al. |
| 5,456,261 A | 10/1995 | Luczyk |
| 5,458,623 A | 10/1995 | Lu et al. |
| 5,503,160 A | 4/1996 | Pering et al. |
| 5,509,927 A | 4/1996 | Epstein et al. |
| 5,520,191 A | 5/1996 | Karlsson et al. |
| 5,531,767 A | 7/1996 | Fain |
| 5,545,186 A | 8/1996 | Olson et al. |
| 5,620,471 A | 4/1997 | Duncan |
| 5,630,425 A | 5/1997 | Panescu et al. |
| 5,634,468 A | 6/1997 | Platt et al. |
| 5,645,070 A | 7/1997 | Turcott |
| 5,682,900 A | 11/1997 | Arand et al. |
| 5,683,425 A | 11/1997 | Hauptmann |
| 5,712,801 A | 1/1998 | Turcott |
| 5,713,367 A | 2/1998 | Arnold et al. |
| 5,738,105 A | 4/1998 | Kroll |
| 5,741,312 A | 4/1998 | Vonk et al. |
| 5,755,736 A | 5/1998 | Gillberg et al. |
| 5,766,225 A | 6/1998 | Kramm |
| 5,772,692 A | 6/1998 | Armstrong |
| 5,776,168 A | 7/1998 | Gunderson |
| 5,779,645 A | 7/1998 | Olson et al. |
| 5,792,065 A | 8/1998 | Xue et al. |
| 5,795,303 A | 8/1998 | Swanson et al. |
| 5,817,133 A | 10/1998 | Houben |
| 5,819,741 A | 10/1998 | Karlsson et al. |
| 5,827,197 A | 10/1998 | Bocek et al. |
| 5,843,133 A | 12/1998 | Routh et al. |
| 5,848,972 A | 12/1998 | Triedman et al. |
| 5,857,977 A | 1/1999 | Caswell et al. |
| 5,873,897 A | 2/1999 | Armstrong et al. |
| 5,891,170 A | 4/1999 | Nitzsche et al. |
| 5,935,081 A | 8/1999 | Kadhiresan |
| 5,954,662 A | 9/1999 | Swanson et al. |
| 5,978,707 A | 11/1999 | Krig et al. |
| 6,108,578 A | 8/2000 | Bardy et al. |
| 6,151,524 A | 11/2000 | Krig et al. |
| 6,169,918 B1 | 1/2001 | Haefner et al. |
| 6,178,350 B1 | 1/2001 | Olson et al. |
| 6,179,865 B1 | 1/2001 | Hsu et al. |
| 6,212,428 B1 | 4/2001 | Hsu et al. |
| 6,223,078 B1 | 4/2001 | Marcovecchio |
| 6,230,055 B1 | 5/2001 | Sun et al. |
| 6,230,059 B1 | 5/2001 | Duffin |
| 6,266,554 B1 | 7/2001 | Hsu et al. |
| 6,275,732 B1 | 8/2001 | Hsu et al. |
| 6,308,095 B1 | 10/2001 | Hsu et al. |
| 6,312,388 B1 | 11/2001 | Marcovecchio et al. |
| 6,317,632 B1 | 11/2001 | Krig et al. |
| 6,405,083 B1 | 6/2002 | Rockwell et al. |
| 6,421,563 B1 | 7/2002 | Sullivan et al. |
| 6,430,435 B1 | 8/2002 | Hsu et al. |
| 6,434,417 B1 | 8/2002 | Lovett |
| 6,449,503 B1 | 9/2002 | Hsu |
| 6,456,871 B1 | 9/2002 | Hsu et al. |
| 6,477,404 B1 | 11/2002 | Yonce et al. |
| 6,480,733 B1 | 11/2002 | Turcott |
| 6,484,055 B1 | 11/2002 | Marcovecchio |
| 6,493,579 B1 | 12/2002 | Gilkerson et al. |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,522,917 B1 | 2/2003 | Hsu et al. |
| 6,522,925 B1 | 2/2003 | Gilkerson et al. |
| 6,526,313 B2 | 2/2003 | Sweeney et al. |
| 6,618,619 B1 | 9/2003 | Florio et al. |
| 6,622,046 B2 | 9/2003 | Fraley et al. |
| 6,658,283 B1 | 12/2003 | Bomzin et al. |
| 6,658,286 B2 | 12/2003 | Seim |
| 6,671,548 B1 | 12/2003 | Mouchawar et al. |
| 6,687,540 B2 | 2/2004 | Marcovecchio |
| 6,708,058 B2 | 3/2004 | Kim et al. |
| 6,728,572 B2 | 4/2004 | Hsu et al. |
| 6,745,068 B2 | 6/2004 | Koyrakh et al. |
| 6,760,615 B2 | 7/2004 | Ferek-Petric |
| 6,766,190 B2 | 7/2004 | Ferek-Petric |
| 6,889,081 B2 | 5/2005 | Hsu |
| 6,892,094 B2 | 5/2005 | Ousdigian et al. |
| 6,959,212 B2 | 10/2005 | Hsu et al. |
| 6,978,177 B1 | 12/2005 | Chen et al. |
| 7,031,764 B2 | 4/2006 | Schwartz et al. |
| 7,039,463 B2 | 5/2006 | Marcovecchio |
| 7,162,298 B2 | 1/2007 | Ideker et al. |
| 7,203,535 B1 | 4/2007 | Hsu et al. |
| 7,228,176 B2 | 6/2007 | Smith et al. |
| 7,515,956 B2 | 4/2009 | Thompson |
| 7,558,631 B2 | 7/2009 | Cowan et al. |
| 7,565,195 B1 | 7/2009 | Kroll et al. |
| 7,634,313 B1 | 12/2009 | Kroll et al. |
| 7,647,109 B2 | 1/2010 | Hastings et al. |
| 7,751,890 B2 | 7/2010 | McCabe et al. |
| 7,761,150 B2 | 7/2010 | Ghanem et al. |
| 7,937,135 B2 | 5/2011 | Ghanem et al. |
| 7,991,471 B2 | 8/2011 | Ghanem et al. |
| 7,996,087 B2 | 8/2011 | Cowan et al. |
| 8,457,742 B2 | 6/2013 | Jacobson |
| 8,571,678 B2 | 10/2013 | Wang |
| 8,744,572 B1 | 6/2014 | Greenhut et al. |
| 8,923,963 B2 | 12/2014 | Bonner et al. |
| 9,072,914 B2 | 7/2015 | Greenhut et al. |
| 2002/0002389 A1 | 1/2002 | Bradley et al. |
| 2002/0032469 A1 | 3/2002 | Marcovecchio |
| 2002/0035335 A1 | 3/2002 | Schauerte |
| 2002/0049474 A1 | 4/2002 | Marcovecchio et al. |
| 2002/0072778 A1 | 6/2002 | Guck et al. |
| 2002/0087091 A1 | 7/2002 | Koyrakh et al. |
| 2002/0091333 A1 | 7/2002 | Hsu et al. |

(56) References Cited

U.S. PATENT DOCUMENTS

| | | |
|---|---|---|
| 2002/0107552 A1 | 8/2002 | Krig et al. |
| 2002/0123768 A1 | 9/2002 | Gilkerson et al. |
| 2002/0123769 A1 | 9/2002 | Panken et al. |
| 2002/0143370 A1 | 10/2002 | Kim |
| 2002/0147407 A1 | 10/2002 | Seim |
| 2002/0147474 A1 | 10/2002 | Seim et al. |
| 2002/0183637 A1 | 12/2002 | Kim et al. |
| 2002/0183639 A1 | 12/2002 | Sweeney et al. |
| 2002/0198461 A1 | 12/2002 | Hsu et al. |
| 2003/0004552 A1 | 1/2003 | Plombon et al. |
| 2003/0050563 A1 | 3/2003 | Suribhotla et al. |
| 2003/0060849 A1 | 3/2003 | Hsu |
| 2003/0069609 A1 | 4/2003 | Thompson |
| 2003/0083586 A1 | 5/2003 | Ferek-Petric |
| 2003/0083587 A1 | 5/2003 | Ferek-Petric |
| 2003/0083703 A1 | 5/2003 | Zhu et al. |
| 2003/0100923 A1 | 5/2003 | Bjorling et al. |
| 2003/0105491 A1 | 6/2003 | Gilkerson et al. |
| 2003/0109792 A1 | 6/2003 | Hsu et al. |
| 2003/0114889 A1 | 6/2003 | Huvelle et al. |
| 2003/0120316 A1 | 6/2003 | Spinelli et al. |
| 2003/0181818 A1 | 9/2003 | Kim et al. |
| 2003/0208238 A1 | 11/2003 | Weinberg et al. |
| 2004/0015090 A1 | 1/2004 | Sweeney et al. |
| 2004/0093035 A1 | 5/2004 | Schwartz et al. |
| 2004/0116820 A1 | 6/2004 | Daum et al. |
| 2004/0116972 A1 | 6/2004 | Marcovecchio |
| 2004/0127806 A1 | 7/2004 | Sweeney et al. |
| 2004/0176694 A1 | 9/2004 | Kim et al. |
| 2005/0010257 A1 | 1/2005 | Lincoln et al. |
| 2005/0149134 A1 | 7/2005 | McCabe et al. |
| 2005/0149135 A1 | 7/2005 | Krig et al. |
| 2005/0159781 A1 | 7/2005 | Hsu |
| 2005/0197674 A1 | 9/2005 | McCabe et al. |
| 2005/0256544 A1 | 11/2005 | Thompson |
| 2006/0015148 A1 | 1/2006 | McCabe et al. |
| 2006/0074330 A1 | 4/2006 | Smith et al. |
| 2006/0122527 A1 | 6/2006 | Marcovecchio |
| 2006/0135999 A1 * | 6/2006 | Bodner .................. A61N 1/056 607/4 |
| 2006/0241701 A1 | 10/2006 | Markowitz et al. |
| 2006/0265018 A1 * | 11/2006 | Smith .................... A61N 1/372 607/14 |
| 2006/0281998 A1 | 12/2006 | Li |
| 2007/0088394 A1 | 4/2007 | Jacobson |
| 2007/0088397 A1 | 4/2007 | Jacobson |
| 2008/0045850 A1 | 2/2008 | Phillips |
| 2010/0069986 A1 | 3/2010 | Stahl et al. |
| 2010/0118798 A1 | 5/2010 | Chun et al. |
| 2010/0228308 A1 | 9/2010 | Cowan et al. |
| 2011/0071586 A1 | 3/2011 | Jacobson |
| 2011/0190835 A1 | 8/2011 | Brockway et al. |
| 2012/0109235 A1 | 5/2012 | Jacobson |
| 2012/0109236 A1 | 5/2012 | Jacobsen et al. |
| 2012/0316613 A1 | 12/2012 | Keefe et al. |
| 2013/0066169 A1 | 3/2013 | Rys et al. |
| 2013/0231710 A1 | 9/2013 | Jacobson |
| 2014/0121719 A1 | 5/2014 | Bonner et al. |
| 2014/0121720 A1 | 5/2014 | Bonner et al. |
| 2014/0214104 A1 | 7/2014 | Greenhut et al. |

FOREIGN PATENT DOCUMENTS

| | | |
|---|---|---|
| EP | 0360412 A1 | 3/1990 |
| EP | 0401962 A2 | 12/1990 |
| EP | 0469817 A2 | 2/1992 |
| EP | 0506230 A1 | 9/1992 |
| EP | 0554208 A2 | 8/1993 |
| EP | 0597459 A2 | 5/1994 |
| EP | 0617980 A2 | 10/1994 |
| EP | 0711531 A1 | 5/1996 |
| EP | 0744190 A2 | 11/1996 |
| EP | 0748638 A2 | 12/1996 |
| EP | 0784996 A1 | 7/1997 |
| EP | 0848965 A2 | 6/1998 |
| EP | 0879621 A2 | 11/1998 |
| EP | 0919256 A1 | 6/1999 |
| EP | 0993842 A1 | 4/2000 |
| EP | 1112756 A2 | 7/2001 |
| JP | 2009518115 A | 5/2009 |
| WO | 9302746 A1 | 2/1993 |
| WO | 9401173 A1 | 1/1994 |
| WO | 9739681 A1 | 10/1997 |
| WO | 9739799 A1 | 10/1997 |
| WO | 9825669 A1 | 6/1998 |
| WO | 9840010 A1 | 9/1998 |
| WO | 9848891 A1 | 11/1998 |
| WO | 9853879 A1 | 12/1998 |
| WO | 9915232 A1 | 4/1999 |
| WO | 0053089 A1 | 9/2000 |
| WO | 0059573 A1 | 10/2000 |
| WO | 0113993 A1 | 3/2001 |
| WO | 0126733 A1 | 4/2001 |
| WO | 03047690 A2 | 6/2003 |
| WO | 2005089643 A1 | 9/2005 |
| WO | 2006020198 A2 | 2/2006 |
| WO | 2006020198 A3 | 5/2006 |
| WO | 2006049767 A1 | 5/2006 |
| WO | 2006124833 A2 | 11/2006 |
| WO | 2014120769 A1 | 8/2014 |

OTHER PUBLICATIONS

Hughes et al., "The Effects of Electrode Position on the Detection of the Transvenous Cardiac Electrogram", PACE, 3(6): 651-655, Nov. 1980.

International Search Report and Written Opinion for Application No. PCT/US2005/035057, 17 pages, dated Feb. 1, 2006.

Kinoshita et al., "Letter to the Editor", Journal of Electrocardiology, 29(3): 255-256, Jul. 1996.

Leitch et al., "Feasibility of an Implantable Arrhythmia Monitor", PACE, 15(12): 2232-2235, Dec. 1992.

Mazur et al., "Functional Similarity Between Electrograms Recorded from an Implantable Cardioverter Defibrillator Emulator and the Surface Electrocardiogram", PACE, 24(1): 34-40, Jan. 2001.

Medtronic, "Marquis™ DR 7274 Dual Chamber Implantable Cardioverter Defibrillator", Reference Manual, 426 pgs., Feb. 2002.

Morris et al., "Detection of Atrial Arrhythmia for Cardiac Rhythm Management by Implantable Devices", Journal of Electrocardiology, vol. 33, Supplement 1, pp. 133-139, 2000.

Theres et al., "Electrogram Signals Recorded from Acute and Chronic Pacemaker Implantation Sites in Pacemaker Patients", PACE, 21(1): 11-17, Jan. 1998.

Kruse, et al., "Detecting and Distinguishing Cardiac Pacing Artifacts," Analog Dialogue 46-11, Nov. 2012, 6 pages.

Notice of Acceptance for Patent Application No. 2015279939, 3 pages, dated Mar. 28, 2018.

* cited by examiner

SYSTEMS AND METHODS FOR TREATING CARDIAC ARRHYTHMIAS

CROSS-REFERENCES TO RELATED APPLICATIONS

This application claims the benefit of U.S. Provisional Application No. 61/926,068, filed Jan. 10, 2014, the complete disclosure of which is herein incorporated by reference.

TECHNICAL FIELD

The present disclosure generally relates to systems, devices, and methods for detecting cardiac arrhythmias and, more specifically to multiple device systems, methods, and devices for detecting and identifying cardiac arrhythmias.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices.

SUMMARY

The present disclosure relates generally to systems and methods for coordinating detection and/or treatment of abnormal heart activity using multiple implanted devices within a patient. It is contemplated that the multiple implanted devices may include, for example, pacemakers, defibrillators, diagnostic devices, and/or any other suitable implantable devices, as desired.

In one example, a method for delivering anti-tachycardia pacing therapy to a heart of a patient may include: in a first one of a plurality of implantable medical devices, determining to deliver anti-tachycardia pacing therapy to the heart of the patient, communicating a message from the first one of the plurality of implantable medical devices to a second one of the plurality of implantable medical devices, the message instructing the second one of the plurality of implantable medical devices to deliver anti-tachycardia pacing therapy to the heart, and in response to receiving the message, the second one of the plurality of implantable medical devices delivering anti-tachycardia pacing therapy to the heart of the patient.

In another example, an implantable medical device system for delivering anti-tachycardia pacing therapy to a heart of a patient may include a first implantable medical device and a second implantable medical device. At least one of the first implantable medical device and the second implantable medical device is configured to deliver anti-tachycardia pacing therapy to the heart of the patient. The first implantable medical device may determine that delivery of anti-tachycardia pacing therapy is desirable, and then may communicate a message to the second implantable medical device. The second implantable medical device may be configured to deliver anti-tachycardia pacing therapy to the heart in response to receiving the message.

In another example, a method of delivering electrical stimulation therapy to a heart of a patient may determine, by a first one of a plurality of implantable medical devices, a presence of an arrhythmia. In response to determining a presence of an arrhythmia, the first one of a plurality of implantable medical devices may then determine that delivery of anti-tachycardia pacing therapy to the heart of the patient is desirable. The first one of a plurality of implantable medical devices may then begin charging a capacitor of a shock channel of the first implantable medical device, and may communicate to a second one of the plurality of implantable medical devices a message to deliver anti-tachycardia pacing therapy. In response to receiving the message from the first one of a plurality of implantable medical devices, the second one of the plurality of implantable medical devices may deliver anti-tachycardia pacing therapy to the heart of the patient during the charging of the capacitor of the first implantable medical device. In some cases, the first one of a plurality of implantable medical devices may be a subcutaneous implantable cardioverter-defibrillator (SICD), and the second one of the plurality of implantable medical devices may be a leadless pacemaker.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
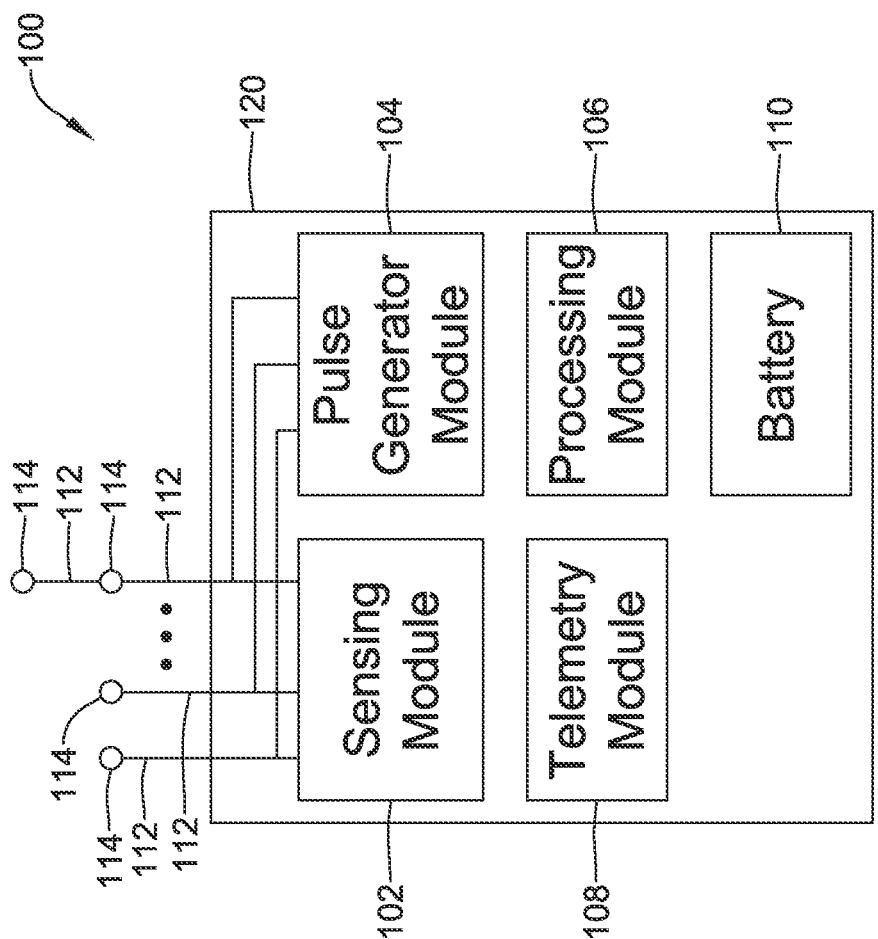
FIG. 1 illustrates a block diagram of an exemplary medical device that may be used in accordance with various examples of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart is almost completely desynchronized and the heart pumps very little to no blood.

Many medical device systems have been developed to assist patients who experience such abnormalities. For example, systems have been developed to sense intrinsic cardiac electrical signals and, based on the sensed electrical signals, determine whether the patient is suffering from one or more arrhythmias. Such systems may also include the ability to deliver electrical stimulation to the heart of the patient in order to treat the detected arrhythmias. In one example, some medical device systems include the ability to identify when the heart is beating at too low of a rate, termed bradycardia. Such systems may deliver electrical stimulation therapy, or "pacing pulses", that cause the heart to contract at a higher, safer rate. Some medical device systems are able to determine when a heart is beating at too fast of a rate, termed tachycardia. Such systems may further include one or more anti-tachycardia pacing (ATP) therapies. One such ATP therapy includes delivering electrical stimulation pulses to the heart at a rate faster than the intrinsically generated signals. Although this may temporarily cause the heart to beat faster, such a stimulation protocol may cause the heart to contract in response to the delivered pacing pulses as opposed to the intrinsically generated signals. The ATP therapy may then slow down the rate of the delivered pacing pulses, thereby reducing the heart rate to a lower, safer level.

Other medical device systems may be able to detect fibrillation states and asynchronous contractions. For example, based on the sensed signals, some systems may be able to determine when the heart is in a fibrillation state. Such systems may further be configured to treat such fibrillation states with electrical stimulation therapy. One such therapy includes deliver of a relatively large amount of electrical energy to the heart (a "defibrillation pulse") with the goal of overpowering any intrinsically generated signals. Such a therapy may "reset" the heart, from an electrical standpoint, which may allow for normal electrical processes to take over. Other medical systems may be able to sense that intrinsically generated signals are generated at differing times or that the heart conducts such signals at differing rates. These abnormalities may result in an unsynchronized, inefficient cardiac contraction. The system may further include the ability to administer one or more cardiac resynchronization therapies (CRTs). One such CRT may include delivering electrical stimulation to the heart at differing locations on and/or within the heart. Such methods may help the disparate parts of the heart to contract near simultaneously, or in a synchronized manner if the system delivers the electrical stimulation to the disparate locations at differing times.

The present disclosure relates generally to systems and methods for coordinating detection and/or treatment of abnormal heart activity using multiple implanted devices within a patient. In some instances, a medical device system may include a plurality of devices for detecting cardiac arrhythmias and delivering electrical stimulation therapy. For example, illustrative systems may include devices such as subcutaneous cardioverter-defibrillators (S-ICD), external cardioverter-defibrillators, implantable cardiac pacemakers (ICP), leadless cardiac pacemakers (LCPs), and/or diagnostic only devices (devices that may sense cardiac electrical signals and/or determine arrhythmias but do not deliver electrical stimulation therapies).

FIG. 1 illustrates a block diagram of an exemplary medical device 100 (referred to hereinafter as, MD 100) that may be used in accordance with various examples of the present disclosure. In some cases, the MD 100 may be used for sensing intrinsic cardiac activity, determining occurrences of arrhythmias, and delivering electrical stimulation in response to determining an occurrence of an arrhythmia. In some instances, MD 100 can be implanted within a patient's body, at a particular location (e.g., in close proximity to the patient's heart), to sense and/or regulate the cardiac activity of the heart. In other examples, MD 100 may be located externally to a patient to sense and/or regulate the cardiac activity of the heart. In one example, cardiac contractions generally result from electrical signals that are intrinsically generated by a heart. These electrical signals conduct through the heart tissue, causing the muscle cells of the heart to contract. MD 100 may include features that allow MD 100 to sense such electrical signals and/or other physical parameters (e.g. mechanical contraction, heart sounds, blood pressure, blood-oxygen levels, etc.) of the heart. Such electrical signals and/or physical properties may be considered "cardiac activity." MD 100 may include the ability to determine occurrences of arrhythmias based on the sensed cardiac activity. In some examples, MD 100 may be able to deliver electrical stimulation to the heart in order to treat any detected arrhythmias. For example, MD 100 may be configured to deliver electrical stimulation, pacing pulses, defibrillation pulses, and/or the like in order to implement one or more therapies, such as bradycardia therapy, ATP therapy, CRT, defibrillation, or other electrical stimulation therapies.

FIG. 1 is an illustration of one example medical device 100. The illustrative MD 100 may include a sensing module 102, a pulse generator module 104, a processing module 106, a telemetry module 108, and a battery 110, all housed within a housing 120. MD 100 may further include leads 112, and electrodes 114 attached to housing 120 and in electrical communication with one or more of the modules 102, 104, 106, and 108 housed within housing 120.

Leads 112 may be connected to and extend away from housing 120 of MD 100. In some examples, leads 112 are implanted on or within the heart of the patient. Leads 112 may contain one or more electrodes 114 positioned at various locations on leads 112 and distances from housing 120. Some leads 112 may only include a single electrode 114 while other leads 112 may include multiple electrodes 114. Generally, electrodes 114 are positioned on leads 112 such that when leads 112 are implanted within the patient, one or more electrodes 114 are in contact with the patient's cardiac tissue. Accordingly, electrodes 114 may conduct intrinsically generated electrical signals to leads 112. Leads 112 may, in turn, conduct the received electrical signals to one or more modules 102, 104, 106, and 108 of MD 100. In a similar manner, MD 100 may generate electrical stimulation, and leads 112 may conduct the generated electrical stimulation to electrodes 114. Electrodes 114 may then conduct the electrical signals to the cardiac tissue of the patient. When discussing sensing intrinsic signals and delivering electrical stimulation, this disclosure may consider such conduction implicit in those processes.

Sensing module 102 may be configured to sense the cardiac electrical activity of the heart. For example, sensing module 102 may be connected to leads 112 and electrodes 114 through leads 112 and sensing module 102 may be configured to receive cardiac electrical signals conducted through electrodes 114 and leads 112. In some examples, leads 112 may include various sensors, such as accelerometers, blood pressure sensors, heart sound sensors, blood-oxygen sensors, and other sensors which measure physiological parameters of the heart and/or patient. In other examples, such sensors may be connected directly to sensing module 102 rather than to leads 112. In any case, sensing module 102 may be configured to receive such signals produced by any sensors connected to sensing module 102, either directly or through leads 112. Sensing modules 102 may additionally be connected to processing module 106 and may be configured to communicate such received signals to processing module 106.

Pulse generator module 104 may be connected to electrodes 114. In some examples, pulse generator module 104 may be configured to generate an electrical stimulation signals to provide electrical stimulation therapy to the heart. For example, pulse generator module 104 may generate such a signal by using energy stored in battery 110 within MD 100. Pulse generator module 104 may be configured to generate electrical stimulation signals in order to provide one or multiple of a number of different therapies. For example, pulse generator module 104 may be configured to generate electrical stimulation signals to provide bradycardia therapy, ATP therapy, cardiac resynchronization therapy, fibrillation therapy, and other electrical stimulation therapies. Bradycardia therapy may include generating and delivering pacing pulses at a rate faster than the intrinsically generated electrical signals in order to try to increase the heart rate. Tachycardia therapy may include ATP therapy as described herein. Cardiac resynchronization therapy may include CRT therapy also described herein. Fibrillation therapy may include delivering a fibrillation pulse to try to override the heart and stop the fibrillation state. In other examples, pulse generator 104 may be configured to generate electrical stimulation signals to provide electrical stimulation therapies different than those described herein to treat one or more detected arrhythmias.

Processing module 106 can be configured to control the operation of MD 100. For example, processing module 106 may be configured to receive electrical signals from sensing module 102. Based on the received signals, processing module 106 may be able to determine occurrences of arrhythmias. Based on any determined arrhythmias, processing module 106 may be configured to control pulse generator module 104 to generate electrical stimulation in accordance with one or more therapies to treat the determined one or more arrhythmias. Processing module 106 may further receive information from telemetry module 108. In some examples, processing module 106 may use such received information in determining whether an arrhythmia is occurring or to take particular action in response to the information. Processing module 106 may additionally control telemetry module 108 to send information to other devices.

In some examples, processing module 106 may include a pre-programmed chip, such as a very-large-scale integration (VLSI) chip or an application specific integrated circuit (ASIC). In such embodiments, the chip may be pre-programmed with control logic in order to control the operation of MD 100. By using a pre-programmed chip, processing module 106 may use less power than other programmable circuits while able to maintain basic functionality, thereby increasing the battery life of MD 100. In other examples, processing module 106 may include a programmable microprocessor. Such a programmable microprocessor may allow a user to adjust the control logic of MD 100, thereby allowing for greater flexibility of MD 100 than when using a pre-programmed chip. In some examples, processing module 106 may further include a memory circuit and processing module 106 may store information on and read information from the memory circuit. In other examples, MD 100 may include a separate memory circuit (not shown) that is in communication with processing module 106, such that processing module 106 may read and write information to and from the separate memory circuit.

Telemetry module 108 may be configured to communicate with devices such as sensors, other medical devices, or the like, that are located externally to MD 100. Such devices may be located either external or internal to the patient's body. Irrespective of the location, external devices (i.e. external to the MD 100 but not necessarily external to the patient's body) can communicate with MD 100 via telemetry module 108 to accomplish one or more desired functions. For example, MD 100 may communicate sensed electrical signals to an external medical device through telemetry module 108. The external medical device may use the communicated electrical signals in determining occurrences of arrhythmias. MD 100 may additionally receive sensed electrical signals from the external medical device through telemetry module 108, and MD 100 may use the received sensed electrical signals in determining occurrences of arrhythmias. In other examples, the various devices of the system may communicate instructions to coordinate delivering of electrical stimulation therapy. Telemetry module 108 may be configured to use one or more methods for communicating with external devices. For example, telemetry module 108 may communicate via radiofrequency (RF) signals, inductive coupling, optical signals, acoustic signals, conducted communication signals, or any other signals suitable for communication. Communication techniques between MD 100 and external devices will be discussed in further detail with reference to FIG. 3 below.

Battery 110 may provide a power source to MD 100 for its operations. In one example, battery 110 may be a non-rechargeable lithium-based battery. In other examples, the non-rechargeable battery may be made from other suitable materials known in the art. Because, in examples where MD 100 is an implantable device, access to MD 100 may be limited, it is necessary to have sufficient capacity of the battery to deliver sufficient therapy over a period of treatment such as days, weeks, months, or years. In other examples, battery 110 may a rechargeable lithium-based battery in order to facilitate increasing the useable lifespan of MD 100.

In general, MD 100 may be similar to one of a number of existing medical devices. For example, MD 100 may be similar to various implantable medical devices. In such examples, housing 120 of MD 100 may be implanted in a transthoracic region of the patient. Housing 120 may generally include any of a number of known materials that are safe for implantation in a human body and may, when implanted, hermetically seal the various components of MD 100 from fluids and tissues of the patient's body.

In some examples, MD 100 may be an implantable cardiac pacemaker (ICP). In such an example, MD 100 may have one or more leads, for example leads 112, which are implanted on or within the patient's heart. The one or more leads 112 may include one or more electrodes 114 that are in contact with cardiac tissue and/or blood of the patient's heart. MD 100 may also be configured to sense intrinsically generated cardiac electrical signals and determine, for example, one or more cardiac arrhythmias based on analysis of the sensed signals. MD 100 may further be configured to deliver CRT, ATP therapy, bradycardia therapy, defibrillation therapy and/or other therapy types via leads 112 implanted within the heart.

In some instances, MD 100 may be a subcutaneous cardioverter-defibrillator (S-ICD). In such examples, one of leads 112 may include a subcutaneously implanted lead. In some cases, MD 100 may be configured to sense intrinsically generated cardiac electrical signals and determine one or more cardiac arrhythmias based on analysis of the sensed signals. MD 100 may further be configured to deliver one or more defibrillation pulses in response to determining an arrhythmia.

Figure 2:
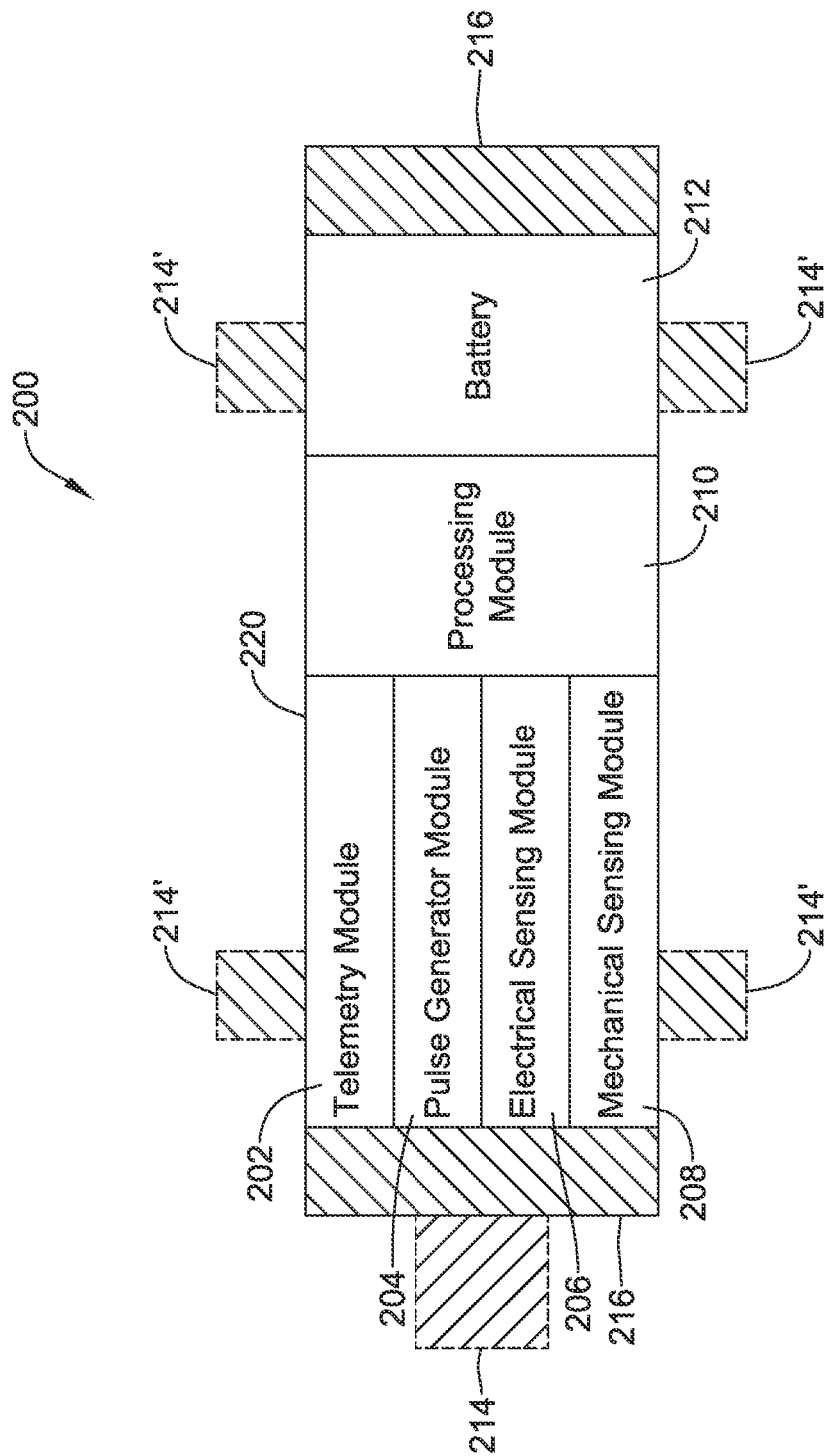
FIG. 2 illustrates an exemplary leadless cardiac pacemaker (LCP) having electrodes, according to one example of the present disclosure.

In still other examples, MD 100 may be a leadless cardiac pacemaker (LCP—described more specifically with respect to FIG. 2). In such examples, MD 100 may not include leads 112 that extend away from housing 120. Rather, MD 100 may include electrodes 114 coupled relative to the housing 120. In these examples, MD 100 may be implanted on or within the patient's heart at a desired location, and may be configured to deliver CRT, ATP therapy, bradycardia therapy, and/or other therapy types via electrodes 114.

In some instances, MD 100 may be a diagnostic-only device. In some cases, MD 100 may be configured to sense, or receive, cardiac electrical signals and/or physical parameters such as mechanical contraction, heart sounds, blood pressure, blood-oxygen levels, etc. MD 100 may further be configured to determine occurrences of arrhythmias based on the sensed or received cardiac electrical signals and/or physical parameters. In one example, MD 100 may do away with pulse generation module 104, as MD 100 may not be configured to deliver electrical stimulation in response to determining an occurrence of an arrhythmia. Rather, in order to respond to detected cardiac arrhythmias, MD 100 may be part of a system of medical devices. In such a system, MD 100 may communicate information to other devices within the system and one or more of the other devices may take action, for example delivering electrical stimulation therapy, in response to the receive information from MD 100. Additionally, the term pulse generator, for example when describing a device, may be used to describe any such device that is capable of delivering electrical stimulation therapy to the heart, such as an ICD, ICP, LCP, or the like.

In some examples, MD 100 may not be an implantable medical device. Rather, MD 100 may be a device external to the patient's body, and may include skin-electrodes that are placed on a patient's body. In such examples, MD 100 may be able to sense surface cardiac electrical signals (e.g. electrical signals that are generated by the heart or device implanted within a patient's body and conducted through the body to the skin). In such examples, MD 100 may still be configured to deliver various types of electrical stimulation therapy. In other examples, however, MD 100 may be a diagnostic-only device.

FIG. 2 is an illustration of an exemplary leadless cardiac pacemaker (LCP) 200. In the example shown, LCP 200 may include all of the modules and components of MD 100, except that LCP 200 may not include leads 112. As can be seen in FIG. 2, LCP 200 may be a compact device with all components housed within LCP 200 or directly on housing 220. As illustrated in FIG. 2, LCP 200 may include telemetry module 202, pulse generator module 204, processing module 210, and battery 212. Such components may have a similar function to the similarly named modules and components as discussed in conjunction with MD 100 of FIG. 1.

In some examples, LCP 200 may include electrical sensing module 206 and mechanical sensing module 208. Electrical sensing module 206 may be similar to sensing module 102 of MD 100. For example, electrical sensing module 206 may be configured to receive electrical signals generated intrinsically by the heart. Electrical sensing module 206 may be in electrical connection with electrodes 214, which may conduct the intrinsically generated electrical signals to electrical sensing module 206. Mechanical sensing module 208 may be configured to receive one or more signals representative of one or more physiological parameters of the heart. For example, mechanical sensing module 208 may include, or be in electrical communication with one or more sensors, such as accelerometers, blood pressure sensors, heart sound sensors, blood-oxygen sensors, and other sensors which measure physiological parameters of the patient. Although described with respect to FIG. 2 as separate sensing modules, in some examples, electrical sensing module 206 and mechanical sensing module 208 may be combined into a single module.

In at least one example, each of modules 202, 204, 206, 208, and 210 illustrated in FIG. 2 may be implemented on a single integrated circuit chip. In other examples, the illustrated components may be implemented in multiple integrated circuit chips that are in electrical communication with one another. All of modules 202, 204, 206, 208, and 210 and battery 212 may be encompassed within housing 220. Housing 220 may generally include any material that is known as safe for implantation within a human body and may hermetically seal modules 202, 204, 206, 208, and 210 and battery 212 from fluids and tissues when LCP 200 is implanted within a patient.

As depicted in FIG. 2, LCP 200 may include electrodes 214, which can be secured relative to housing 220 but exposed to the tissue and/or blood surrounding the LCP 200. As such, electrodes 214 may be generally disposed on either end of LCP 200 and may be in electrical communication with one or more of modules 202, 204, 206, 208, and 210. In some examples, electrodes 214 may be connected to housing 220 only through short connecting wires such that electrodes 214 are not directly secured relative to housing 220. In some examples, LCP 200 may additionally include one or more electrodes 214'. Electrodes 214' may be positioned on the sides of LCP 200 and increase the number of electrodes by which LCP 200 may sense cardiac electrical activity and/or deliver electrical stimulation. Electrodes 214 and/or 214' can be made up of one or more biocompatible conductive materials such as various metals or alloys that are known to be safe for implantation within a human body. In some instances, electrodes 214 and/or 214' connected to LCP 200 may have an insulative portion that electrically isolates the electrodes 214 from, adjacent electrodes, the housing 220, and/or other materials.

To implant LCP 200 inside patient's body, an operator (e.g., a physician, clinician, etc.), may need to fix LCP 200 to the cardiac tissue of the patient's heart. To facilitate fixation, LCP 200 may include one or more anchors 216. Anchor 216 may be any one of a number of fixation or anchoring mechanisms. For example, anchor 216 may include one or more pins, staples, threads, screws, helix, tines, and/or the like. In some examples, although not shown, anchor 216 may include threads on its external surface that may run along at least a partial length of anchor 216. The threads may provide friction between the cardiac tissue and the anchor to help fix anchor 216 within the cardiac tissue. In other examples, anchor 216 may include other structures such as barbs, spikes, or the like to facilitate engagement with the surrounding cardiac tissue.

The design and dimensions of MD 100 and LCP 200, as shown in FIGS. 1 and 2, respectively, can be selected based on various factors. For example, if the medical device is for implant on the endocardial tissue, such as is sometimes the case of an LCP, the medical device can be introduced through a femoral vein into the heart. In such instances, the dimensions of the medical device may be such as to be navigated smoothly through the tortuous path of the vein without causing any damage to surrounding tissue of the vein. According to one example, the average diameter of the femoral vein may be between about 4 mm to about 8 mm in width. For navigation to the heart through the femoral vein, the medical device can have a diameter of at less than 8 mm. In some examples, the medical device can have a cylindrical shape having a circular cross-section. However, it should be noted that the medical device can be made of any other suitable shape such as rectangular, oval, etc. A flat, rectangular-shaped medical device with a low profile may be desired when the medical device is designed to be implanted subcutaneously.

FIGS. 1 and 2 above described various examples of MD 100. In some examples, a medical device system may include more than one medical device. For example, multiple medical devices 100/200 may be used cooperatively to detect and treat cardiac arrhythmias and/or other cardiac abnormalities. Some example systems will be described below in connection with FIGS. 3-10. In such multiple device systems, it may be desirable to have a medical device communicate with another medical device, or at least receive various communication signals from another medical device.

Figure 3:
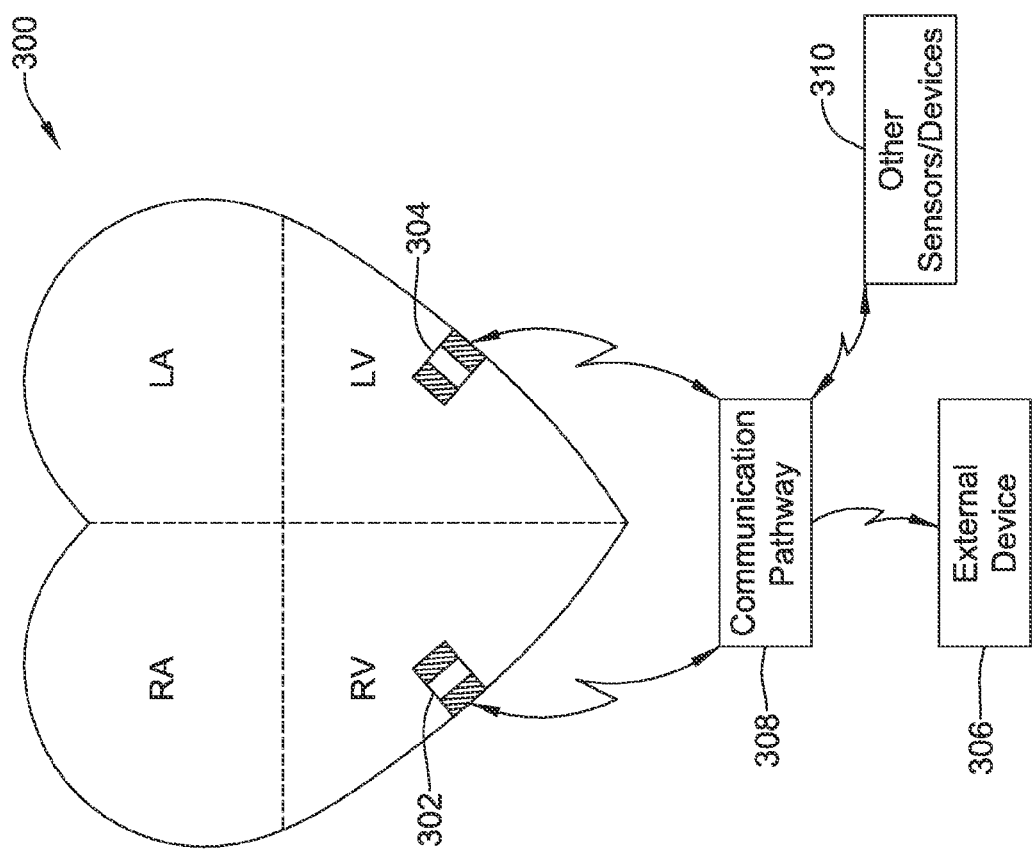
FIG. 3 is a schematic diagram of an exemplary medical system that includes multiple leadless cardiac pacemakers (LCPs) and/or other devices in communication with one another of the present disclosure.

FIG. 3 illustrates an example of a medical device system and a communication pathway via which multiple medical devices may communicate. In the example shown, medical device system 300 may include LCPs 302 and 304, external medical device 306, and other sensors/devices 310. External device 306 may be any of the devices described previously with respect to MD 100. Other sensors/devices 310 may also be any of the devices described previously with respect to MD 100. In other examples, other sensors/devices 310 may include a sensor, such as an accelerometer or blood pressure sensor, or the like. In still other examples, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one example, external device 306 may receive such signals and, based on the received signals, determine an occurrence of an arrhythmia. In some cases, external device 306 may communicate such determinations to one or more other devices 302/304, 306, and 310 of system 300. Additionally, one or more other devices 302/304, 306, and 310 of system 300 may take action based on the communicated determination of an arrhythmia, such as by delivering a suitable electrical stimulation. This description is just one of many reasons for communication between the various devices of system 300.

Communication pathway 308 may represent one or more of various communication methods. For example, the devices of system 300 may communicate with each other via RF signals, inductive coupling, optical signals, acoustic signals, or any other signals suitable for communication and communication pathway 308 may represent such signals.

In at least one example, communicated pathway 308 may represent conducted communication signals. Accordingly, devices of system 300 may have components that allow for conducted communication. In examples where communication pathway 308 includes conducted communication signals, devices of system 300 may communicate with each other by sensing electrical communication pulses delivered into the patient's body by another device. The patient's body may conduct these electrical communication pulses to the other devices of system 300. In such examples, the delivered electrical communication pulses may differ from the electrical stimulation pulses of any of the above described electrical stimulation therapies. For example, the devices of system 300 may deliver such electrical communication pulses at a voltage level that is sub-threshold. That is, the voltage amplitude of the delivered electrical communication pulses may be low enough as to not capture the heart (e.g.

not cause a contraction). Although, in some circumstances, one or more delivered electrical communication pulses may capture the heart. Additionally, in other circumstances, delivered electrical stimulation pulses may not capture the heart, yet are not electrical communication pulses. In some cases, the delivered electrical communication pulses may be modulated (e.g. pulse width modulated), or the timing of the delivery of the communication pulses may be modulates, to encode the communicated information. These are just some examples.

As mentioned above, some example systems may employ multiple devices for determining occurrences of arrhythmias, and/or for delivering electrical stimulation therapy in response to determining one or more arrhythmias. FIGS. 3-10 describe various example systems that may use multiple devices in order to determine occurrences of arrhythmias and/or deliver electrical stimulation therapy. However, FIGS. 3-10 should not be viewed as limiting examples. For example, FIGS. 3-10 describe how various multiple device systems may coordinate to detect and/or treat various arrhythmias. However, any combinations of devices such as that described with respect to MD 100 and LCP 200 may be used in concert with the below described techniques for detecting and/or treating arrhythmias.

Figure 4:
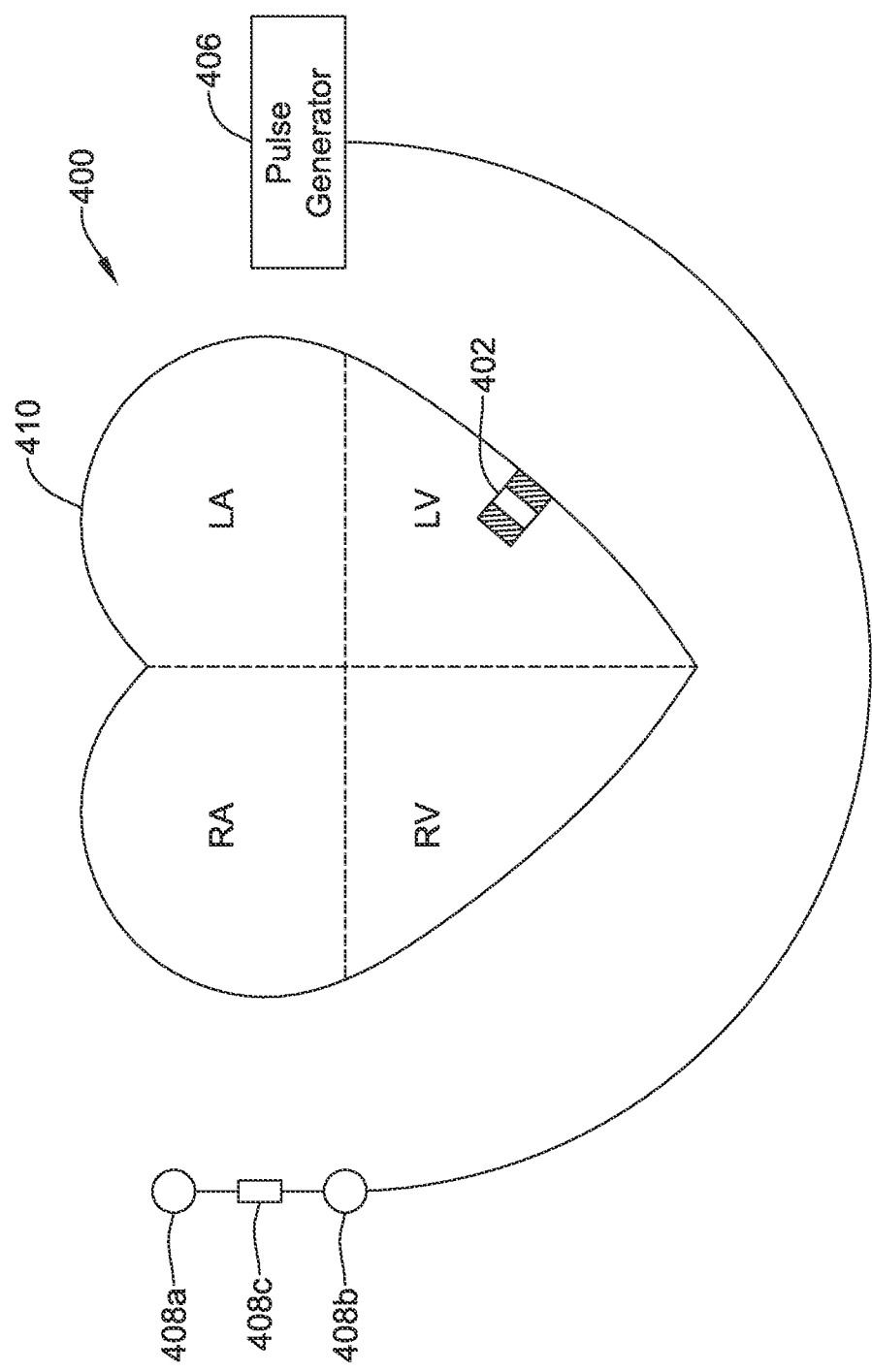
FIG. 4 is a schematic diagram of a system including an LCP and another medical device, in accordance with yet another example of the present disclosure.

FIG. 4 illustrates an example medical device system 400 that includes an LCP 402 and a pulse generator 406. In some examples, pulse generator 406 may be either an external cardioverter-defibrillator or an ICD. For example, pulse generator 406 may be such devices as described previously with respect to MD 100. In some examples, pulse generator 406 may be an S-ICD. In examples where pulse generator 406 is an external cardioverter-defibrillator, electrodes 408a, 408b, and 408c may be skin electrodes that reside on the patient's body. In examples where pulse generator 406 is an S-ICD, electrodes 408a, 408b, and 408c may be attached to a subcutaneous lead that is implanted within the patient's body proximate, but not on or within the heart 410.

As shown, LCP 402 may be implanted within heart 410. Although LCP 402 is depicted as being implanted within the left ventricle (LV) of heart 410, in other examples, LCP 402 may be implanted within a different chamber of the heart 410. For example, LCP 402 may be implanted within the left atrium (LA) of heart 410 or the right atrium (RA) of heart 410. In other examples, LCP 402 may be implanted within the right ventricle (RV) of heart 410.

In any event, LCP 402 and pulse generator 406 may operate together to determine occurrences of cardiac arrhythmias of heart 410. In some instances, devices 402 and 406 may operate independently to sense cardiac activity of heart 410. As described above, cardiac activity may include sensed cardiac electrical signals and/or sensed physiological parameters. In such examples, each of LCP 402 and pulse generator 406 may operate to determine occurrences of arrhythmias independently of one another based on the independently sensed cardiac activity. When a first of LCP 402 or pulse generator 406 makes a first determination of an arrhythmia, that first device may communicate the first determination to the second device. If the second device of system 400 also makes a determination of an arrhythmia, e.g. a second determination of an arrhythmia, based on its own sensed cardiac activity, the arrhythmia may be confirmed and the system 400 may begin to deliver appropriate electrical stimulation therapy to heart 410. In this manner, both devices 402 and 406 of system 400 may be used to determine an occurrence of an arrhythmia. In some examples, when only one of devices 402 or 406 determines an occurrence of an arrhythmia, and the other does not, system 400 may still begin to deliver appropriate electrical stimulation therapy to heart 410.

In other examples, only one of devices 402 and 406 actively senses cardiac activity and determines occurrences of arrhythmias. For example, when the actively sensing device (e.g. LCP 402) determines an occurrence of an arrhythmia, the actively sensing device may communicate the determination to the other device (e.g. Pulse Generator 406) of system 400. System 400 may then begin to deliver appropriate electrical stimulation therapy to heart 410. In another example, the device which actively senses cardiac activity may communicate the sensed cardiac activity to the other device. Then, based on the received cardiac activity, the other device may determine an occurrence of an arrhythmia. System 400 may then begin to deliver appropriate electrical stimulation therapy to heart 410. In some of these examples, the other device may additionally communicate the determination of an arrhythmia to the actively sensing device.

In still other examples, only a first of devices 402 or 406 continuously senses cardiac actively. The first device (e.g. Pulse Generator 406) may continually determine, based on the sensed cardiac activity, occurrences of arrhythmias. In such examples, when the first device determines an occurrence of an arrhythmia, the first device may communicate the determination to the second device (e.g. LCP 402). Upon receiving a determination of an occurrence of an arrhythmia, the second device may begin to sense cardiac activity. Based on its sensed cardiac activity, the second device may also determine an occurrence of an arrhythmia. In such examples, only after the second device also determines an occurrence of an arrhythmia, system 400 may begin to deliver appropriate electrical stimulation therapy to heart 410.

In some examples, determining an occurrence of an arrhythmia may include determining a beginning of an arrhythmia, and system 400 may be configured to determine when to begin to deliver electrical stimulation therapy. In some examples, determining an occurrence of an arrhythmia may include determining an end of an arrhythmia. In such examples, system 400 may be configured to also determine when to cease to deliver electrical stimulation therapy.

In examples where system 400 operates to deliver appropriate electrical stimulation therapy to heart 410, if the determined arrhythmia is a fibrillation, pulse generator 406 may operate to deliver a defibrillation pulse to heart 410. In examples where the determined arrhythmia is a tachycardia, LCP 402 may deliver ATP therapy to heart 410. In examples where the determined arrhythmia is a bradycardia, LCP 402 may deliver bradycardia therapy to heart 410. In examples where the determined arrhythmia is un-synchronized contractions, LCP 402 may deliver CRT to heart 410. In some examples, pulse generator 406 and LCP 402 may coordinate to deliver electrical stimulation therapy to heart 410 in accordance with one or more of the techniques described below with respect to FIGS. 11-16.

Figure 5:
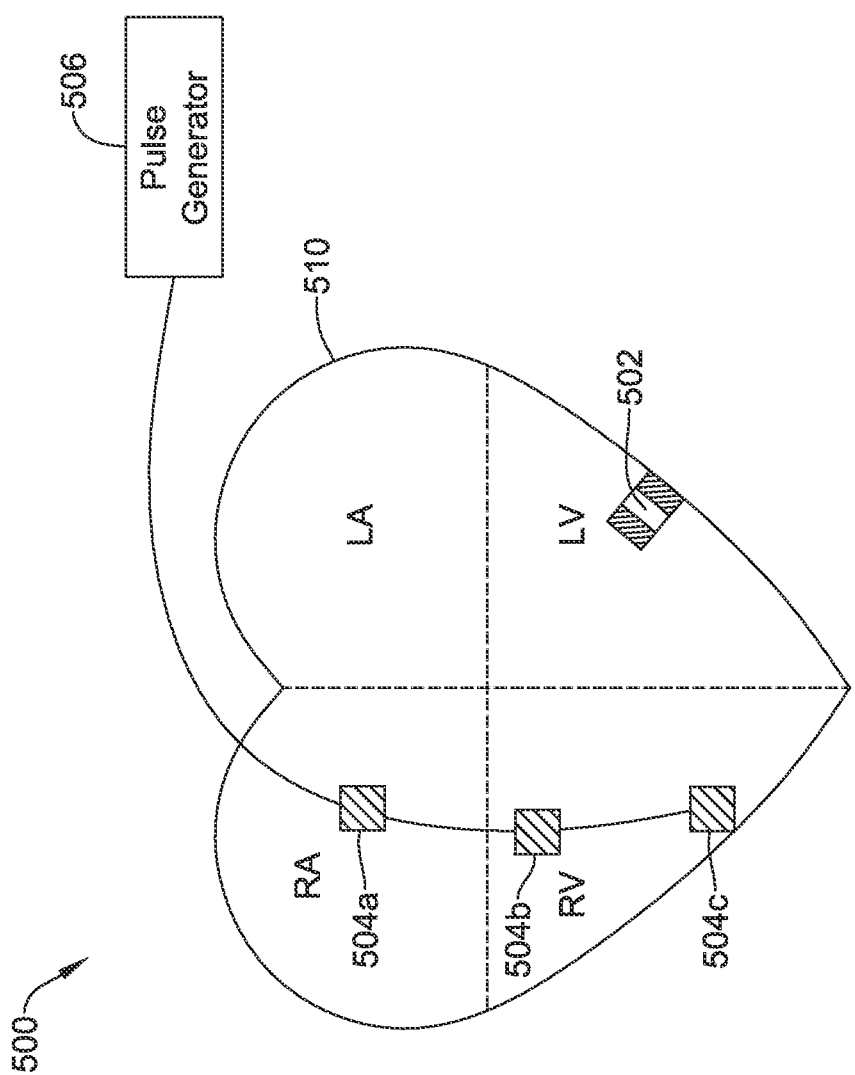
FIG. 5 is a schematic diagram of the a system including an LCP and another medical device, in accordance with another example of the present disclosure.

FIG. 5 illustrates an example medical device system 500 that includes an LCP 502 and a pulse generator 506. In this example, pulse generator 506 may be an implantable cardiac pacemaker (ICP). For example, pulse generator 506 may be an ICP such as that described previously with respect to MD 100. In examples where pulse generator 506 is an ICP, electrodes 504a, 504b, and 504c may be implanted on or within the right ventricle and/or right atrium of heart 510 via one or more leads.

LCP 502 may be implanted within heart 510. Although LCP 502 is depicted implanted within the left ventricle (LV)

of the heart 510, in some instances, LCP 502 may be implanted within a different chamber of the heart 510. For example, LCP 502 may be implanted within the left atrium (LA) of heart 510 or the right atrium (RA) of heart 510. In other examples, LCP 502 may be implanted within the right ventricle (RV) of heart 510.

In any event, LCP 502 and pulse generator 506 may operate together to determine occurrences of cardiac arrhythmias of heart 510. In some instances, devices 502 and 506 may operate independently to sense cardiac activity of heart 510. As described above, cardiac activity may include sensed cardiac electrical signals and/or sensed physiological parameters. In some cases, each of LCP 502 and pulse generator 506 may operate to determine occurrences of arrhythmias independently based on the independently sensed cardiac activity. When a first of LCP 502 or pulse generator 506 makes a first determination of an arrhythmia, that first device may communicate the first determination to the second device. If the second device of system 500 also makes a determination of an arrhythmia, e.g. a second determination of an arrhythmia, based on its own sensed cardiac activity, system 500 may confirm the arrhythmia and may begin to deliver appropriate electrical stimulation therapy to heart 510. In this manner, both devices 502 and 506 of system 500 may be used to determine an occurrence of an arrhythmia. In some instances, when only a single one of devices 502 or 506 determines an occurrence of an arrhythmia, system 500 may also begin to deliver appropriate electrical stimulation therapy to heart 510.

In some examples, only one of devices 502 and 506 may actively sense cardiac activity and determine occurrences of arrhythmias. For example, when the actively sensing device (e.g. pulse generator 506) determines an occurrence of an arrhythmia, the actively sensing device may communicate the determination to the other device (e.g. LCP 502) of system 500. System 500 may then begin to deliver appropriate electrical stimulation therapy to heart 510. In some examples, the device which actively senses cardiac activity may communicate the sensed cardiac activity to the other device. Then, based on the received cardiac activity, the other device may sense for and determine an occurrence of an arrhythmia. System 500 may then begin to deliver appropriate electrical stimulation therapy to heart 510. In some instances, the other device may additionally communicate the determination of an arrhythmia to the actively sensing device.

In still other examples, only a first of devices 502 or 506 may continuously sense cardiac actively. The first device may additionally continually determine, based on the sensed cardiac activity, occurrences of arrhythmias. In some examples, when the first device determines an occurrence of an arrhythmia, the first device may communicate the determination to the second device. Upon receiving a determination of an occurrence of an arrhythmia, the second device may begin to sense cardiac activity. Based on its sensed cardiac activity, the second device may also determine an occurrence of an arrhythmia. In such examples, only after the second device also determines an occurrence of an arrhythmia, system 500 may begin to deliver appropriate electrical stimulation therapy to heart 510.

In some examples, determining an occurrence of an arrhythmia may include determining a beginning of an arrhythmia, and system 500 may be configured to determine when to begin to deliver electrical stimulation therapy. In some examples, determining an occurrence of an arrhythmia may include determining an end of an arrhythmia. In such examples, system 500 may be configured to determine when to cease to deliver electrical stimulation therapy. In examples where system 500 does not begin to deliver appropriate electrical stimulation therapy to heart 510 until multiple devices determine an occurrence of a cardiac arrhythmia, each of the determinations that do not trigger delivery of electrical stimulation therapy may be termed provisional determinations.

In examples where system 500 operates to deliver appropriate electrical stimulation therapy to heart 510, if the determined arrhythmia is a tachycardia, either pulse generator 506, LCP 502, or both may deliver ATP therapy to heart 510. In examples where the determined arrhythmia is a bradycardia, either pulse generator 506, LCP 502, or both may deliver bradycardia therapy to heart 510. In examples where the determined arrhythmia is un-synchronized contractions, either pulse generator 506, LCP 502, or both may deliver CRT to heart 510. In some examples, pulse generator 506 and LCP 502 may coordinate to deliver electrical stimulation therapy to heart 510 in accordance with one or more of the techniques described below with respect to FIGS. 11-16.

Figure 6:
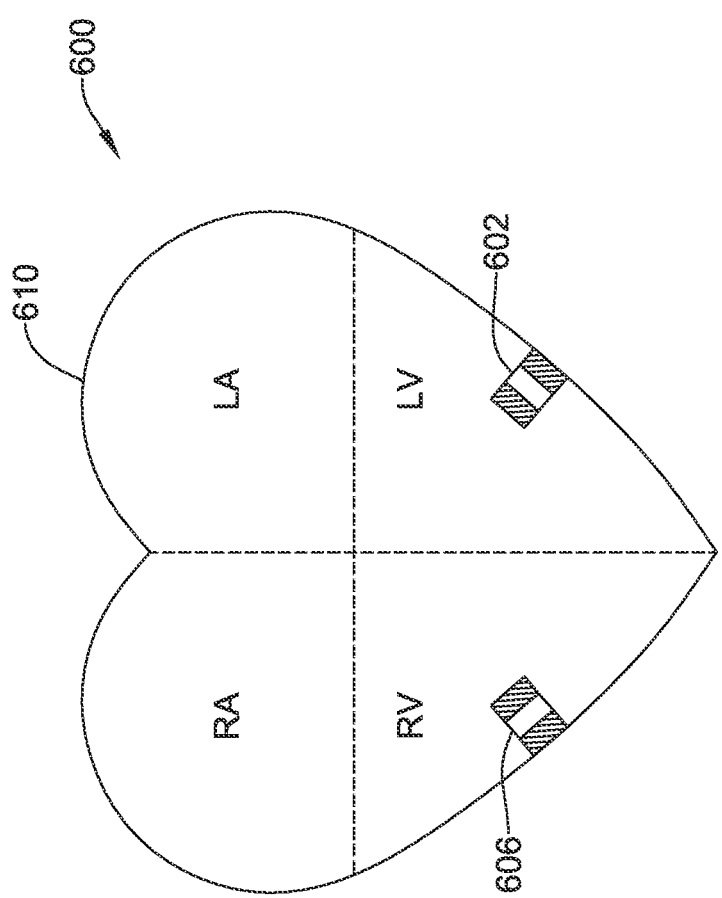
FIG. 6 is a schematic diagram illustrating a multiple leadless cardiac pacemaker (LCP) system in accordance with another example of the present disclosure.

FIG. 6 illustrates an example medical device system 600 that includes LCP 602 and LCP 606. LCP 602 and LCP 606 are shown implanted within heart 610. Although LCPs 602 and 606 are depicted as implanted within the left ventricle (LV) of heart 610 and the right ventricle of heart 610, respectively, in other examples, LCPs 602 and 606 may be implanted within different chambers of heart 610. For example, system 600 may include LCPs 602 and 606 implanted within both atria of heart 610. In other examples, system 600 may include LCPs 602 and 606 implanted within one atrium and one ventricle of heart 610. In more examples, system 600 may include LCPs 602 and 606 implanted within any combination of ventricles and atria. In yet other examples, system 600 may include LCPs 602 and 606 implanted within the same chamber of heart 610.

In any event, and in some examples, LCP 602 and LCP 606 may operate together to determine occurrences of cardiac arrhythmias of heart 610. For example, devices 602 and 606 may operate independently to sense cardiac activity of heart 610. As described above, cardiac activity may include sensed cardiac electrical signals and/or sensed physiological parameters. In such examples, each of LCP 602 and LCP 606 may operate to determine occurrences of arrhythmias independently based on the independently sensed cardiac activity. When a first of LCP 602 or LCP 606 makes a first determination of an arrhythmia, that first device may communicate the first determination to the second device. If the second device of system 600 also makes a determination of an arrhythmia, e.g. a second determination of an arrhythmia, based on its own sensed cardiac activity, system 600 may confirm the arrhythmia and may begin to deliver appropriate electrical stimulation therapy to heart 610. In this manner, both devices 602 and 606 of system 600 may be used to determine an occurrence of an arrhythmia. In some examples, when only a single one of devices 602 or 606 determines an occurrence of an arrhythmia, system 600 may begin to deliver appropriate electrical stimulation therapy to heart 610.

In other examples, only one of devices 602 and 606 may actively sense cardiac activity and determine occurrences of arrhythmias. In some of these examples, when the actively sensing device (e.g. LCP 606) determines an occurrence of an arrhythmia, the actively sensing device may communicate the determination to the other device (e.g. LCP 602) of system 600. System 600 may then begin to deliver appropriate electrical stimulation therapy to heart 610. In some cases, the device which actively senses cardiac activity may communicate the sensed cardiac activity to the other device. Then, based on the received cardiac activity, the other device may determine an occurrence of an arrhythmia. System 600 may then begin to deliver appropriate electrical stimulation therapy to heart 610. In some of these examples, the other device may additionally communicate the determination of an arrhythmia to the actively sensing device and/or to another device.

In some examples, only a first of devices 602 or 606 may continuously sense cardiac actively. The first device may continually determine, based on the sensed cardiac activity, occurrences of arrhythmias. In such examples, when the first device determines an occurrence of an arrhythmia, the first device may communicate the determination to the second device. Upon receiving a determination of an occurrence of an arrhythmia, the second device may begin to sense cardiac activity. Based on its sensed cardiac activity, the second device may also determine an occurrence of an arrhythmia. In such examples, only after the second device also determines an occurrence of an arrhythmia does system 600 begin to deliver appropriate electrical stimulation therapy to heart 610.

In some examples, determining an occurrence of an arrhythmia may include determining a beginning of an arrhythmia, and system 600 may be configured to determine when to begin to deliver electrical stimulation therapy. In some examples, determining an occurrence of an arrhythmia may include determining an end of an arrhythmia. In such examples, system 600 may be configured to also determine when to cease to deliver electrical stimulation therapy. In examples where system 600 does not begin to deliver appropriate electrical stimulation therapy to heart 610 until multiple devices determine an occurrence of a cardiac arrhythmia, each of the determinations that do not trigger delivery of electrical stimulation therapy may be termed provisional determinations.

In examples where system 600 operates to deliver appropriate electrical stimulation therapy to heart 610, if the determined arrhythmia is a tachycardia, either LCP 602, LCP 606, or both may deliver ATP therapy to heart 610. In examples where the determined arrhythmia is a bradycardia, either LCP 602, LCP 606, or both may deliver bradycardia therapy to heart 610. In examples where the determined arrhythmia is un-synchronized contractions, either pulse LCP 602, LCP 606, or both may deliver CRT to heart 610. In some examples, pulse generator 606 and LCP 602 may coordinate to deliver electrical stimulation therapy to heart 610 in accordance with one or more of the techniques described below with respect to FIGS. 11-16.

Although not necessarily described in FIGS. 4-6, one of the two devices of systems 400, 500, or 600 could be a diagnostic-only device. In such examples, after one or more of the devices determined an occurrence of an arrhythmia, the diagnostic-only device may not deliver any electrical stimulation therapy. Rather, electrical stimulation therapy may be delivered by another device in the system that is capable of delivering appropriate electrical stimulation therapy, if desired.

Figure 7:
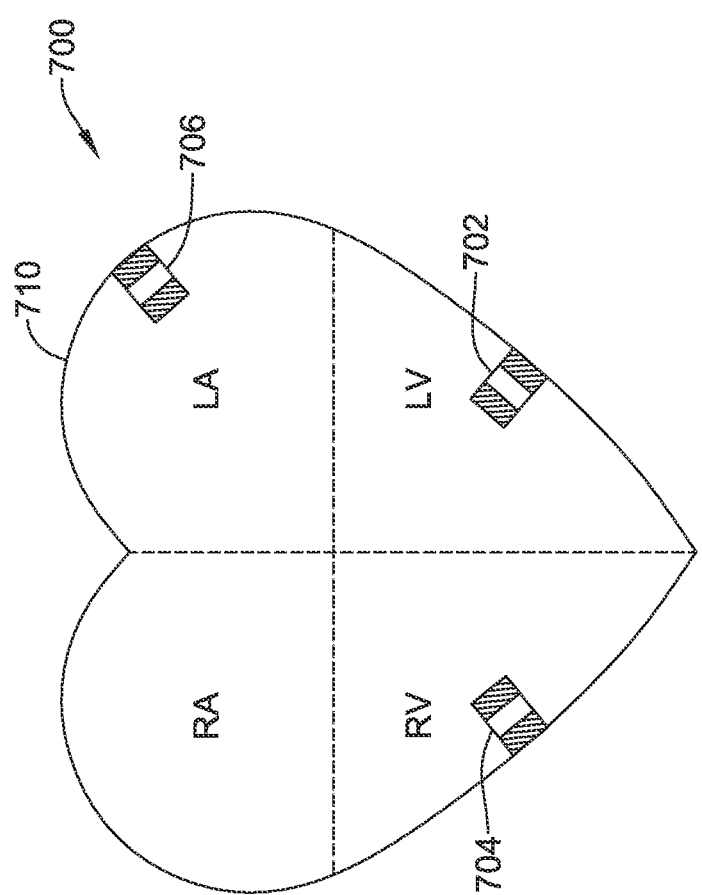
FIG. 7 is a schematic diagram illustrating a multiple leadless cardiac pacemaker (LCP) system, in accordance with yet another example of the present disclosure.

FIG. 7 illustrates an example medical device system 700 with three separate LCPs including LCP 702, LCP 704, and LCP 706. Although system 700 is depicted with LCPs 702, 704, and 706 implanted within the LV, RV, and LA, respectively, other examples may include LCPs 702, 704, and 706 implanted within different chambers of the heart 710. For example, system 700 may include LCPs implanted within both atria and one ventricle of the heart 710. In other examples, system 700 may include LCPs implanted within both ventricles and one atria of heart 710. More generally, it is contemplated that system 700 may include LCPs implanted within any combination of ventricles and atria. In some instances, system 700 may include two or more of LCPs 702, 704, and 706 implanted within the same chamber of the heart 710.

In practice, such a system 700 may operate in accordance with any of the techniques described above with respect to FIGS. 4-6. In some instances, however, system 700 may operate differently, at least to some degree. For example, before system 700 begins to deliver appropriate electrical stimulation therapy to the heart 710, only a majority of LCPs 702, 704, and 706 may need to determine an occurrence of an arrhythmia. For example, in some instances, all of LCPs 702, 704, and 706 may be sensing cardiac activity and determining occurrences of arrhythmias independently. In some cases, only after a majority of LCPs 702, 704, and 706 determined an occurrence of an arrhythmia, may system 700 deliver appropriate electrical stimulation therapy to the heart 710. In some instances, one of the LCP's is designated as the master LCP, and the other slave LCP's may communicate whether they determined an occurrence of an arrhythmia to the master LCP. The master LCP may then determine if a majority of the LCP's 702, 704, and 706 have determined an occurrence of an arrhythmia, and if so, may instruct the delivery of appropriate electrical stimulation therapy to the heart 710. In some instances, the master LCP may instruct particular ones of the LCP's 702, 704, and 706 to deliver electrical stimulation therapy to the heart 710, depending on the type and/or location of the detected arrhythmia.

Alternatively, and in some instances, only a single LCP may need to determine an occurrence of an arrhythmia before system 700 may begin to deliver appropriate electrical stimulation therapy to heart 710. In yet other examples, all three of the LCP's 702, 704, and 706 may need to determine an occurrence of an arrhythmia before system 700 delivers appropriate electrical stimulation therapy to the heart 710.

In some cases, only one LCP 702, 704, and 706 may actively sense cardiac activity and determine an occurrence of an arrhythmia. After determining an occurrence of an arrhythmia, the actively sensing device may communicate the determination to one or both of the other devices. In some cases, one or both of the other devices may then begin sensing for and determining occurrences of arrhythmias. In some instances, when a first one of the other devices determines an occurrence of an arrhythmia, system 700 may begin to deliver appropriate electrical stimulation therapy to heart 710. In other instances, when both of the other devices determine an occurrence of an arrhythmia, system 700 may begin to deliver appropriate electrical stimulation therapy to heart 710.

In some instances, LCPs 702, 704, and 706 may be set up in a daisy-chain configuration. For example, an actively sensing device may send a determination of an arrhythmia to only one of the other two devices (alternatively, only one of the two receiving devices may act upon the received determination from the actively sensing device). The receiving device may then begin actively sensing for and determining occurrences of arrhythmias. Upon determining an occurrence of an arrhythmia, the receiving device may communicate the determination to the last device. The last device may then begin sensing for and determining occurrences of arrhythmias. In some instances, only when the last device determines an occurrence of an arrhythmia does the system 700 begin to deliver appropriate electrical stimulation therapy to heart 710.

Also in accord with the description of systems 400, 500, and 700, in some examples, determining an occurrence of an arrhythmia may include determining a beginning of an arrhythmia, and system 700 may be configured to determine when to begin to deliver electrical stimulation therapy. In some examples, determining an occurrence of an arrhythmia may include determining an end of an arrhythmia. In such examples, system 700 may be configured to determine when to cease delivery of electrical stimulation therapy. In examples where system 700 does not begin to deliver appropriate electrical stimulation therapy to heart 710 until multiple LCP devices determine an occurrence of an arrhythmia, each of the determinations that do not trigger delivery of electrical stimulation therapy may be termed provisional determinations.

In examples where system 700 operates to deliver appropriate electrical stimulation therapy to heart 710, if the determined arrhythmia is a tachycardia, one or more of LCPs 702, 704, and 706 may deliver ATP therapy to heart 710. In examples where the determined arrhythmia is a bradycardia, one or more of LCPs 702, 704, and 706 may deliver bradycardia therapy to heart 710. In examples where the determined arrhythmia is un-synchronized contractions, one or more of LCPs 702, 704, and 706 may deliver CRT to heart 710. It is contemplated that less than all of LCPs 702, 704, and 706 may deliver electrical stimulation therapy in response to the detection of an arrhythmia. For example, only a single of LCPs 702, 704, and 706 may deliver electrical stimulation therapy. In other examples, two of LCPs 702, 704, and 706 may deliver electrical stimulation therapy. In some examples, LCPs 702, 704, and 706 may coordinate to deliver electrical stimulation therapy to heart 710 in accordance with one or more of the techniques described below with respect to FIGS. 11-16.

In accordance with the above described description, one can see how such techniques may be extended to systems that have even more than three LCP devices. For example, in a four LCP device system, any of one, two, three, or four devices may be used to determine an occurrence of an arrhythmia before the system begins to deliver appropriate electrical stimulation therapy. In some such examples, all, some, or one of the LCP devices may initially actively sense and determine the occurrences of arrhythmias. In examples where less than all are initially actively sensing, once one of the actively sensing devices determines an occurrence of an arrhythmia, and communicates that determination to other devices of the system, at least one of the other devices of the system may begin to actively sense cardiac activity and determine occurrences of arrhythmias. Again, the techniques described above may be extended to systems that include any number of LCP devices or other devices, such as five, six, seven, or any other number that is practically feasible for implantation within a patient's body.

Additionally, although described above with respect to three or more LCP devices, the same techniques may be applied to any of the systems described with respect to FIGS. 4-5. For example, any of systems 400 and 500 may further include a third device, such as a second LCP device. In such systems, the three devices may operate in accordance with any of the above described techniques of system 700, with the pulse generator capable of sensing for arrhythmias and/or delivering electrical stimulation therapy. In other examples, any of systems 400 and 500 may include a plurality of additional devices. For example, any of systems 400 and 500 may include three, four, five, or any number of LCP devices that are practical for implantation with a patient in addition to pulse generators 406 and 506. Accordingly, in such examples, the devices may operate together in accordance with any of the above described techniques.

A multiple device system may, in some cases, be capable of delivering more effective electrical stimulation therapy than a single device system. For example, before beginning to deliver electrical stimulation therapy, example systems may determine which of the devices of the system first senses a depolarization wave of the heart. In such examples, such systems may direct the device which senses the depolarization wave first to deliver the electrical stimulation therapy. This may allow such systems to deliver electrical stimulation therapy at a site closer to the origin of an arrhythmia, which may increase the effectiveness of the electrical stimulation therapy.

In the example of system 700, one of the devices of system 700 may determine an occurrence of a tachyarrhythmia, either individually or in addition to provisional determinations by other devices of system 700 in accordance with any of the techniques described above. One of the devices of system 700 (e.g. a master device) may determine to deliver ATP therapy to heart 710 or to determine to direct another device of system 700 to deliver ATP therapy. Before either delivering, or directing another device to deliver ATP therapy, one of the devices of system 700 may determine which device of system 700 first senses an intrinsic cardiac depolarization wave of heart 710. The device that senses such a depolarization wave first may then begin delivery of ATP therapy.

The above description is just one example of how a system may operate to deliver electrical stimulation therapy by the device that senses the intrinsic cardiac depolarization wave of a heart first. In other examples, the type of arrhythmia and therapy may be different. Additionally, as such a feature is not tied to any particular configuration or number of devices, any of the systems described herein may further include such a feature. The only limitation in any system may be whether the devices of the system are capable of delivering the appropriate electrical stimulation therapy.

A multiple device system may be used to help provide discrimination between atrial arrhythmias and ventricular arrhythmias. For instance, example systems described herein may operate differently depending on whether an arrhythmia is an atrial arrhythmia or a ventricular arrhythmia in order to more effectively treat such arrhythmias.

As one illustrative example, one of the devices of system 700 may determine an occurrence of a tachyarrhythmia, either individually or in addition to provisional determinations by other devices of system 700 in accordance with any of the techniques described above. Additionally, a device of system 700 may determine whether the tachycardia is an atrial tachycardia or a ventricular tachycardia. If the tachycardia is an atrial tachycardia, one or more of the devices of system 700 may determine to not deliver electrical stimulation therapy. If the tachycardia is a ventricular tachycardia, one or more of the devices of system 700 may additionally determine whether the rate of the tachycardia is above a threshold and whether the cardiac electrical signal is a polymorphic signal. If the tachycardia rate is below the threshold and the cardiac electrical signal is not a polymorphic signal, one or more of the devices of system 700 may deliver, or direct a different device of system 700 to deliver, ATP therapy to the heart 710. If the tachycardia rate is above the threshold or the cardiac electrical signal is a polymorphic signal, one or more of the devices of system 700 may deliver, or direct a different device of system 700 to deliver, a defibrillation pulse to heart 710. Discriminating between such atrial and ventricular arrhythmias, and responding differently to the different types of arrhythmias, may increase the effectiveness of delivered electrical stimulation therapy and decrease negative outcomes of any delivered electrical stimulation therapy. The above description is just one example of how the disclosed systems may operate to discriminate between various arrhythmias and deliver electrical stimulation therapy in response to the different determined arrhythmias.

Figure 8:
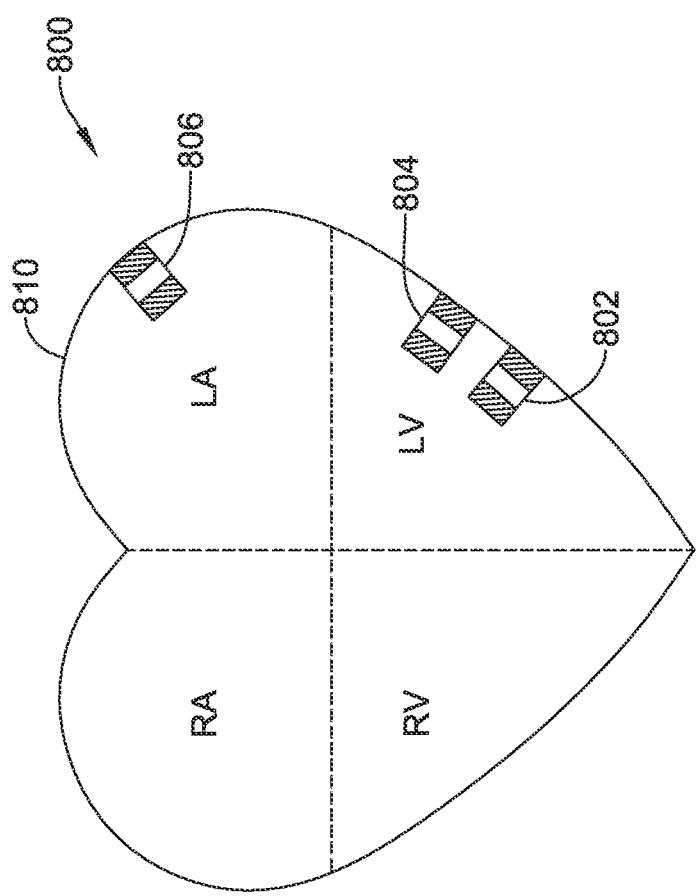
FIG. 8 is a schematic diagram illustrating a multiple leadless cardiac pacemaker (LCP) system where two LCPs are implanted within a single chamber of a heart, in accordance with yet another example of the present disclosure.
Figure 9:
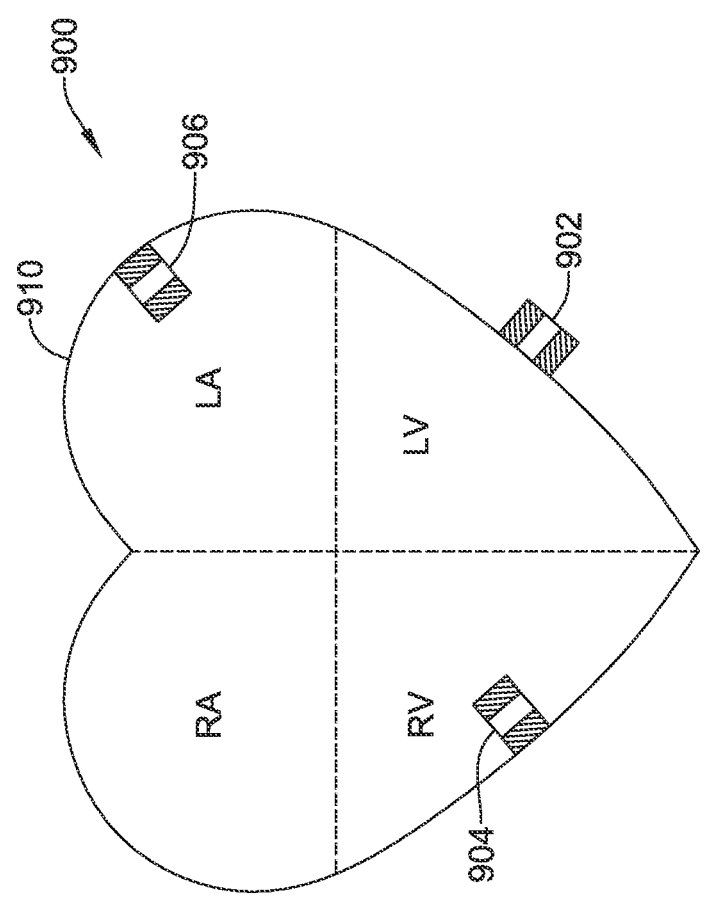
FIG. 9 is a schematic diagram illustrating a multiple leadless cardiac pacemaker (LCP) system where one of the LCPs is implanted on an epicardial surface of a heart, in accordance with another example of the present disclosure.

FIGS. 8 and 9 illustrate other example implantation locations and configurations for a multiple device medical system. For example, medical device system 800 of FIG. 8 shows three LCP devices, LCPs 802, 804, and 806. Two of the LCP devices, LCPs 802 and 804, are shown implanted within a single chamber of heart 810. In other examples, all three devices may be implanted within a single chamber of heart 810. Although two LCP's 802 and 804 are shown implanted within the LV of heart 810, in other examples, any of the chambers of heart 810 may include multiple implanted LCP devices. Implanting multiple devices within a single chamber may enhance the effectiveness of delivered electrical stimulation, as the multiple devices may increase the chances of delivering electrical stimulation therapy near a cardiac site that is an origin of an arrhythmia causing signal. As described previously with respect to the other systems, any of the other system described herein, such as systems 400 and 500 may include one or more devices implanted within a single chamber of the heart, as desired.

Medical device system 900 of FIG. 9 includes an LCP 902 implanted on an epicardial surface of heart 910. LCPs 904 and 906 are shown implanted on an endocardial surface of heart 910. In some instances, one or more additional devices of system 900 may be implanted on an epicardial surface. In some instance, a device implanted on an epicardial surface of a heart may sense intrinsic cardiac electrical signals and/or deliver appropriate electrical stimulation therapy to the heart. Accordingly, any of the systems described herein may include one or more devices implanted on an endocardial surface of a heart, as desired.

Figure 10:
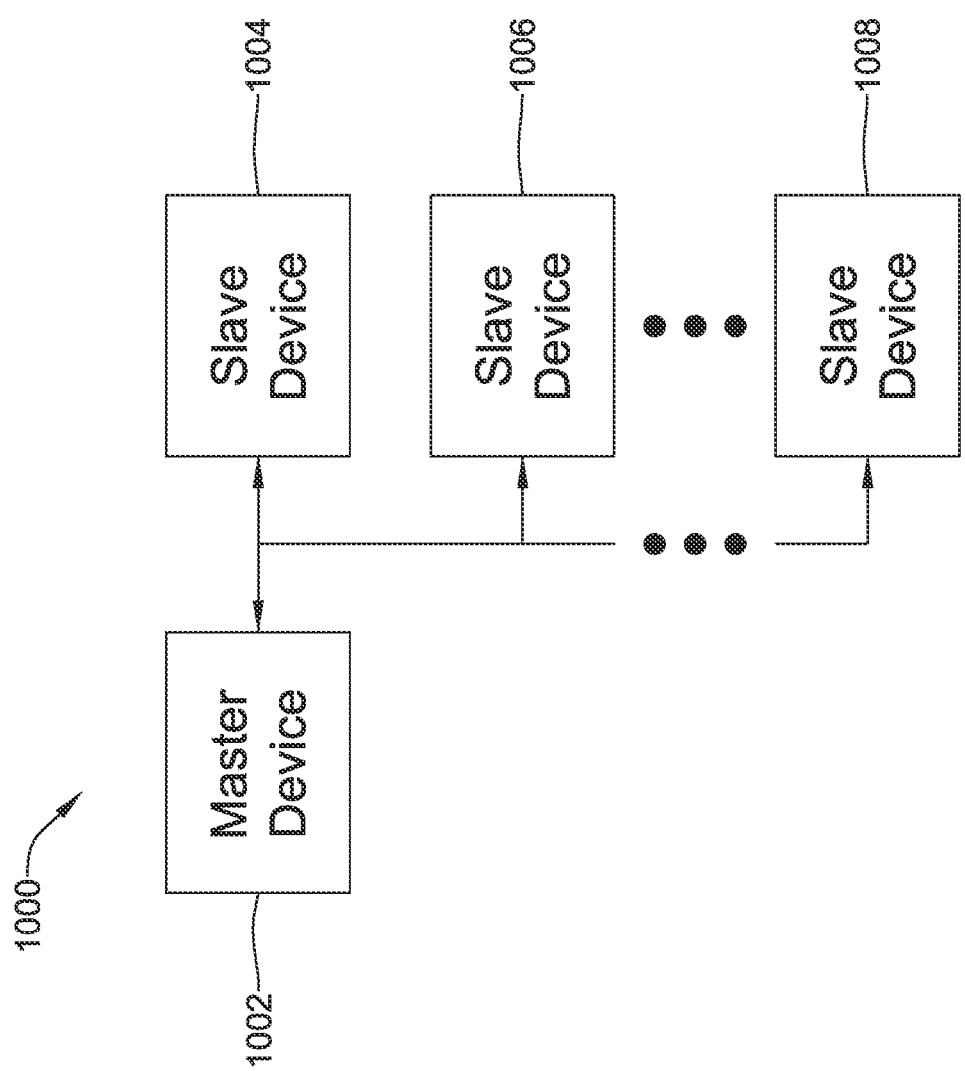
FIG. 10 is a block diagram of an exemplary medical system including a master device and multiple slave devices.

As noted above, in some embodiments, one device in a medical system may act a master device and the other devices may act as slave devices. FIG. 10 is a block diagram of an illustrative medical device system 1000 that includes a master device 1002 and multiple slave devices 1004, 1006, and 1008. In the example shown, the master device 1002 may conductively communicate with the slave devices 1004, 1006, and 1008 through the body of the patient. In other examples, the master and slave devices may communicate via a different communication mechanism, such as through radiofrequency (RF) signals, inductive coupling, optical signals, acoustic signals, or any other suitable for communication mechanism, as desired.

In one example, the master device 1002 may be an ICD device, for example, an ICD or an S-ICD, and may be configured to receive cardiac information from one or more slave devices 1004, 1006, and 1008. In some cases, the slave devices may be LCP's. The communicated cardiac information may include, for example, cardiac electrical signals sensed by the slave devices 1004, 1006, and 1008, preliminary determinations made by the slave devices 1004, 1006, and 1008, or other information sensed or determined by the slave devices 1004, 1006, and 1008. In some examples, master device 1002 may also sense cardiac activity. In such examples, master device 1002 may determine occurrences of arrhythmias based on either its own sensed cardiac activity and/or the received cardiac activity from the slave devices 1004, 1006 and 1008. In some instances, master device 1002 may determine that the cardiac activity from one or multiple devices of system 1000 indicates an occurrence of an arrhythmia. In some cases, although multiple devices of system 1000 may each be sensing cardiac activity, only a single device, such as master device 1002, may make the determination that a cardiac arrhythmia is occurring and that an appropriate electrical stimulation therapy is desired.

In response to determining an occurrence of an arrhythmia, master device 1002 may determine to deliver electrical stimulation therapy. In one example, master device 1002 may determine an appropriate electrical stimulation therapy based on the type of arrhythmia. Additionally, master device 1002 may determine which device or devices should deliver the electrical stimulation therapy. Master device 1002 may direct one or more of the devices, which might include the master device itself, to actually deliver the desired electrical stimulation therapy. Master device 1002 may operate according to any of the previously disclosed techniques. For example, master device 1002 may determine one or more provisional determinations of occurrences of arrhythmias before determining an actual occurrence of an arrhythmia. Master device 1002 may additionally distinguish between atrial and ventricular arrhythmias and determine appropriate electrical stimulation therapy to deliver based on the determined type of arrhythmia. In some examples, master device 1002 may determine which device or devices need to deliver electrical stimulation therapy based on which device or devices sensed the cardiac depolarization wave first of a cardiac cycle.

In some instances, multiple devices of system 1000 may determine occurrences of arrhythmias. For example, slave devices 1004, 1006, and 1008 may each determine occurrences of arrhythmias and may communicate such determinations to master device 1002. In some examples, such determinations may be considered actual or provisional determinations. Based on such received determinations, master device 1002 may determine an occurrence of an arrhythmia, in accordance with any of the previously disclosed techniques. Based on an determination of an arrhythmia, master device 1002 may deliver, and/or direct one or more of slave devices 1004, 1006, and 1008 to deliver, appropriate electrical stimulation therapy.

In some cases, not all of master device 1002 and slave devices 1004, 1006, and 1008 may be actively sensing for an arrhythmia. For instance, as described previously, in some examples only a single, or less than all of master device 1002 and slave devices 1004, 1006, and 1008 may be actively sensing for an arrhythmia. In at least one example, the actively sensing device may be sending cardiac activity to master device 1002. Based on the received cardiac activity, master device 1002 may determine an occurrence of an arrhythmia. After determining an occurrence of an arrhythmia, master device 1002 may direct a second device of system 1000 to begin actively sensing cardiac activity. This second device may additionally communicate sensed cardiac activity to master device 1002. Again, master device 1002 may determine an occurrence of an arrhythmia based on the received cardiac activity from the second device. After making one or more determinations of an occurrence of an arrhythmia, master device 1002 may deliver, or direct one or more of slave devices 1004, 1006, and 1008 to deliver, appropriate electrical stimulation therapy. In other examples, instead of sending sensed cardiac data, the devices may send determinations of occurrences of an arrhythmia to master device 1002. In some cases, master device 1002 may not sense cardiac activity. Rather, master device 1002 may make determinations of occurrences of cardiac arrhythmias based on received cardiac activity and/or determinations from those slave devices that are sensing cardiac activity.

In some cases, master device 1002 may be an LCP device, an external cardioverter-defibrillator, ICP, or diagnostic-only device. In some examples, master device 1002 and the slave devices 1004, 1006, and 1008 may have similar hardware configuration; however, they may have different software installed. In some examples, the slave devices 1004, 1006, and 1008 may be set to a "slave mode" while master device 1002 may be set to a "master mode", even though all devices share the same hardware and software features. Additionally, in some examples, the devices of system 1000 may switch between being configured as a master device and a slave device. For example, an external programmer may connect to any of the devices of such systems and alter the programming of any of the devices of the system, as desired.

Figure 11:
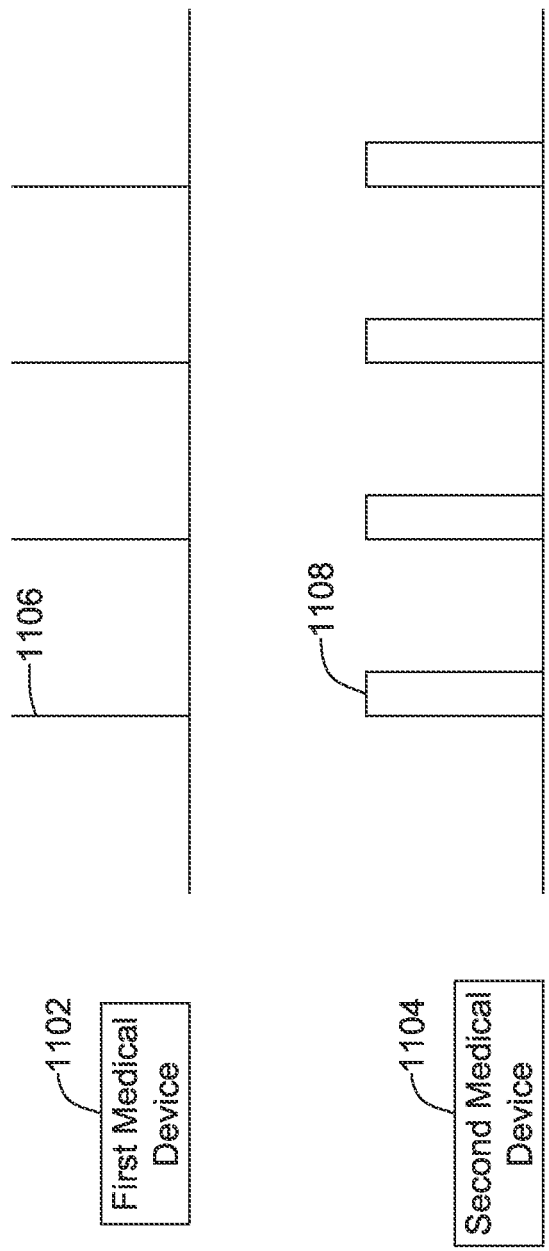
FIG. 11 shows an illustrative timing chart of trigger signals from a first device causing pacing pulses to be delivered by a second device.

FIGS. 11-14 describe various methods and/or techniques by which one or more devices of a medical device system may coordinate to deliver appropriate electrical stimulation therapy to a heart. FIG. 11 illustrates a first technique by which at least two medical devices 1102 and 1104 of a medical device system may coordinate to deliver electrical stimulation therapy. In the example shown in FIG. 11, first medical device 1102 of a medical device system, such as any of system 400, 500, 600, or any other suitable system, may communicate multiple trigger signals 1106 to second medical device 1104 of the system. The one or more trigger signals 1106 may cause second medical device 1108 to deliver electrical stimulation therapy, for example pacing pulses 1108, to the heart. In the example of FIG. 11, first medical device 1102 may send multiple trigger signals 1106, and each trigger signal 1106 may cause the second medical device 1104 to deliver a single pacing pulse 1108.

In some examples, first medical device 1102 may communicate one or more parameters for the pacing pulses 1108 that are to be delivered to the heart by the second medical device 1104. For example, first medical device 1102 may send one or more signals to second medical device 1104 that indicate, for example, a voltage amplitude, a pulse width, a coupling interval (interval from intrinsic heart signal to pacing pulse), and/or other suitable parameter(s) for the corresponding pacing pulse 1108. In some instances, one or more signals may be encoded in the trigger signal 1106, or may be provided in a separate signal. In some cases, each trigger signal 1106, in addition to causing second medical device 1104 to deliver a corresponding pacing pulse 1108, may be encoded with information such as a voltage amplitude and/or pulse width of the corresponding pacing pulse 1108. In some instances, one trigger signal 1106 may be encoded with a voltage amplitude, a pulse width and/or other any other suitable pacing parameters. Thereafter, the second medical device 1104 may deliver subsequent pacing pulses 1108 according to such communicated pacing parameters until the second medical device 1104 receives different parameters from the first medical device 1102.

In some example, such parameters may be communicated to second medical device 1104 prior to the system determining an occurrence of any arrhythmia. For instance, first medical device 1102, or another device, may communicate such parameters to second medical device 1104 at implantation or during or after a programming session. In still other examples, such parameters may be pre-programmed into second medical device 1104, such as at the factory. In these instances, the parameters may be communicated to second medical device 1104 separately from the trigger signals 1106. Although described above with respect to two devices, the technique of FIG. 11 may be extended to systems that include additional devices. For example, in such multiple device systems, a single device may send multiple trigger commands to multiple devices of the system, causing multiple of the devices to deliver corresponding pacing pulses. In such examples, a first device may send such trigger signals at slightly different times to multiple different devices, thereby causing each of the receiving devices to deliver pacing pulses at slightly different times. In another example the first device may send a single trigger single that triggers multiple different devices.

In some instances, a first device may send trigger signals to only one of the other multiple devices. For example, a first device may send trigger signals to the particular device that sensed a depolarization wave of the heart last relative to the other devices of the multiple device system. In still other examples, multiple devices may send trigger signals to multiple other devices, if desired. In some instances, the first device may be a subcutaneous cardioverter-defibrillators (S-ICD), and the other devices may be leadless cardiac pacemakers (LCPs), but this is just one example.

Figure 12:
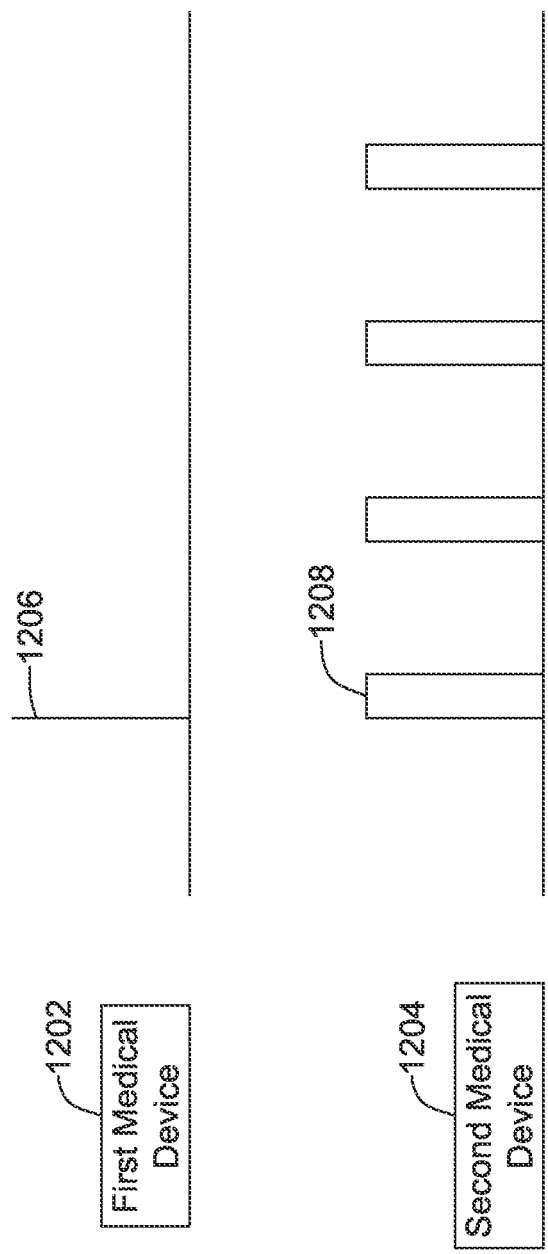
FIG. 12 shows an illustrative timing chart where a trigger signal from a first device causes a second device to deliver a series of pacing pulses.

FIG. 12 shows another illustrative technique by which at least two devices of a medical device system may coordinate to deliver electrical stimulation therapy. In the example of FIG. 12, first medical device 1202 of a system, such as any of system 400, 500, 600, or any other suitable system, may communicate a trigger signal 1206 to a second medical device 1204 of the system. Trigger signal 1206 may cause second medical device 1204 to deliver electrical stimulation therapy, and in the example shown, multiple pacing pulses 1208, to a heart. In FIG. 12, first medical device 1202 may send one trigger signal 1206 to second medical device 1204, which may cause the second medical device 1204 to deliver multiple pacing pulses 1208.

In some examples, first medical device 1202 may communicate one or more parameters for pacing pulses 1208 that are to be delivered by second medical device 1204 to the heart. For example, first medical device 1202 may send one or more signals to second medical device 1204 indicating a voltage amplitude, a pulse width, and/or any other suitable parameters for pacing pulses 1208. Alternatively, or in addition, first medical device 1202 may communicate a pulse train length parameter, a pulse frequency (interval between pacing pulses), a coupling interval and/or other pulse information to the second medical device 1204. The pulse train length parameter may indicate a desired number of pacing pulses 1208 that the second medical device 1204 should deliver in response to receiving a single trigger signal 1206.

In some examples, the one or more signals may be encoded in or on the trigger signal 1206. For example, trigger signal 1206, in addition to causing second medical device 1204 to deliver a train of pacing pulses 1208, may be encoded with information such as voltage amplitude, pulse width, train length, pulse frequency, and/or any other suitable parameters of pacing pulses 1208. In some examples, first medical device 1202 may communicate a delay parameter, which may indicate how quickly second medical device 1204 should begin delivering pacing pulses 1208 after receiving the trigger signal 1206 from the first medical device 1202.

In some examples, such parameters may be communicated to second medical device 1204 prior to the system determining an occurrence of any arrhythmia. For instance, first medical device 1202, or another device, may communicate such parameters to second medical device 1204 at implantation or during or after a programming session. In still other examples, such parameters may be pre-programmed into second medical device 1204, such as at the factory.

In some instances, the first medical device 1202 may communicate a start trigger signal 1206 and a stop trigger signal 1206*a*. For example, a start trigger signal 1206 may cause second medical device 1204 to begin delivering pacing pulses 1208 according to one or more parameters, such as a voltage amplitude parameter, a pulse width parameter, and/or other parameters. First medical device 1202 may subsequently deliver a stop trigger 1206*a* (shown in dashed lines). Such a stop trigger 1206*a* may cause second medical device 1204 to cease delivering pacing pulses 1208. In some examples, after first medical device 1202 delivers a stop trigger 1206*a*, one or more devices of the system may determine whether an arrhythmia is still occurring. In examples where one of the devices of the system does determine that an arrhythmia is still occurring, the first medical device 1302 may communicate another start trigger signal 1206 to second medical device 1204.

Although described above with respect to two devices, the techniques of FIG. 12 may be extended to systems that include additional devices. For example, in such multiple device systems, a single device may send trigger signals 1206 to multiple other devices of the system, causing multiple of the other devices to deliver pacing pulses 1208 according to communicated or stored parameters. For example, in such multiple device systems, a single device may send multiple trigger commands to multiple devices of the system, causing multiple of the devices to deliver corresponding pacing pulses. In such examples, a first device may send such trigger signals at slightly different times to multiple different devices, thereby causing each of the receiving devices to deliver pacing pulses at slightly different times.

In some instances, a first device may send trigger signals to only one of the other multiple devices. For example, a first device may send trigger signals to the particular device that sensed a depolarization wave of the heart last relative to the other devices of the multiple device system. In still other examples, multiple devices may send trigger signals to multiple other devices, if desired. In some instances, the first device may be a subcutaneous cardioverter-defibrillators (S-ICD), and the other devices may be leadless cardiac pacemakers (LCPs), but this is just one example.

Figure 13:
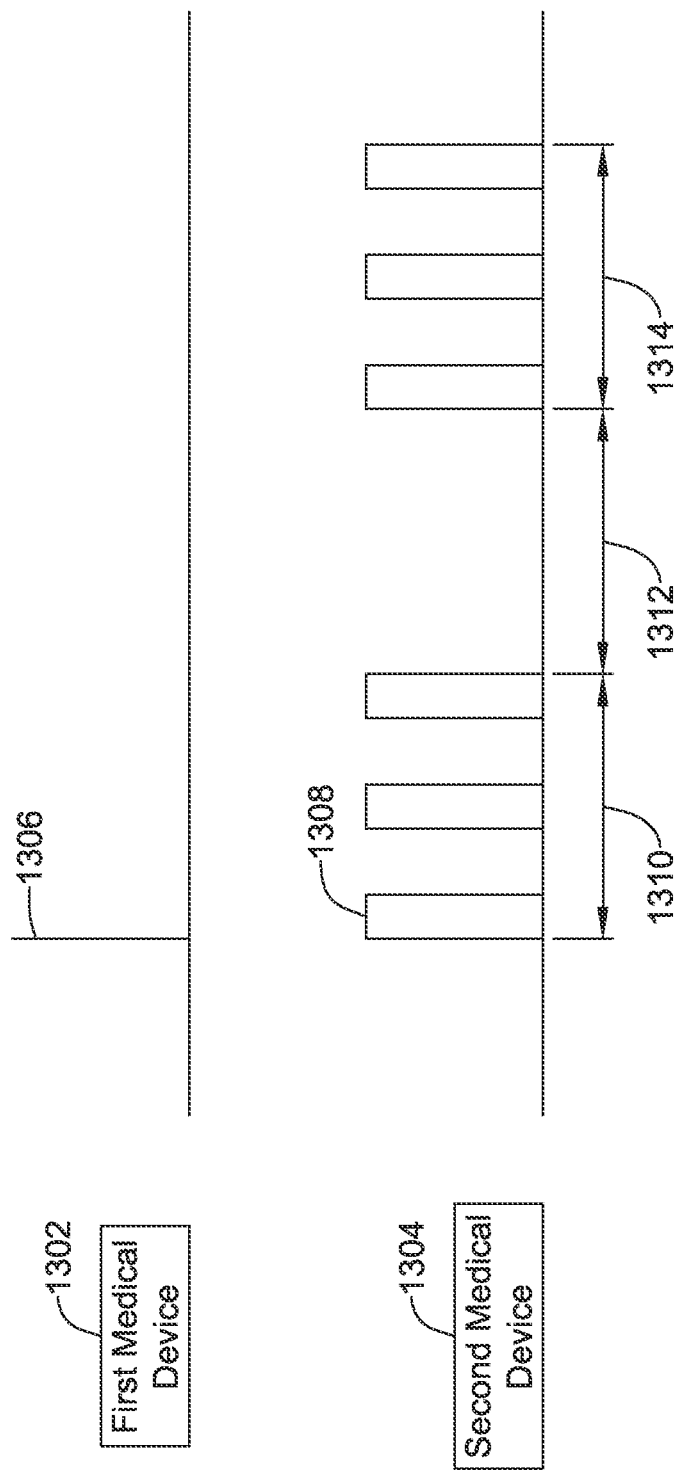
FIG. 13 shows an illustrative timing chart where a trigger signal from a first device causes a second device to deliver pacing pulses in accordance with a therapy protocol.

FIG. 13 shows yet another illustrative technique by which at least two devices of a medical device system may coordinate to deliver electrical stimulation therapy. In the example of FIG. 13, first medical device 1302 of a system, such as any of system 400, 500, 600, or any other suitable system, may communicate a trigger signal 1306 to second medical device 1304 of the system. Trigger signal 1306 may cause the second medical device 1304 to deliver electrical stimulation therapy, for example multiple pacing pulses 1308, to a heart. In the example shown in FIG. 13, first medical device 1302 may send a trigger signal 1306 to second medical device 1304, which may cause the second medical device 1304 to deliver electrical stimulation therapy according to a predefined therapy protocol.

In some examples, first medical device 1302 (or another medical device) may communicate one or more therapy protocols to the second medical device 1304. FIG. 13 illustrates one such therapy protocol. The illustrative therapy protocol depicted in FIG. 13 includes three separate periods, labeled 1310, 1312, and 1314, respectively. The therapy protocol may cause the second medical device 1304 to deliver pacing pulses 1308 during a first time period 1310. The therapy protocol may additionally cause the second medical device 1304 to cease delivering pacing pulses 1308 during a second time period 1312. In some examples, the therapy protocol may additionally cause the first medical device 1302, second medical device 1304, and/or another device of the system to determine if an arrhythmia is still occurring during the second time period 1312. If it is determined that an arrhythmia is still occurring, the illustrative therapy protocol may cause the second medical device 1304 to continue delivering pacing pulses 1308 during a third time period 1314. In some examples the pacing parameters (e.g. pacing pulse interval) are different in time period 1310 than in time period 1314. In examples where none of the devices determines that an arrhythmia is still occurring during the second time period 1312, and this determination is communicated to the second medical device 1304, the therapy protocol may cause the second medical device 1304 to not deliver pacing pulses during the third time period 1314. This is just one example of a therapy protocol that may be communicated to the second medical device 1304. Other examples may include therapy protocols including greater or fewer time periods, and/or different logic dictating when to deliver and not deliver electrical stimulation pulses 1308.

In some instances, a therapy protocol may include parameters for the pacing pulses 1308, such as voltage amplitude, pulse width, pulse train length, and/or parameters. In some cases, such parameters may not be a part of the therapy protocol, but rather may be communicated separately from the therapy protocol. As described above with respect to FIGS. 11 and 12 above, such parameters and/or therapy protocols may be communicated to the second medical device 1304 in a variety of ways. For example, the parameters and/or therapy protocols may be communicated before or along with a trigger signal 1306. In other examples, such parameters may be communicated to the second medical device 1304 prior to the system determining an occurrence of an arrhythmia. For instance, first medical device 1302, or another device, may communicate such parameters to the second medical device 1304 at implantation or during or after a programming session. In still other examples, such parameters may be pre-programmed into second medical device 1304, such as at the factory. In examples where the second medical device 1304 includes multiple stored therapy protocols, whether pre-programmed at the factory or previously communicated to second medical device 1304, first medical device 1302 may simply reference or select which therapy protocol stored in the second medical device 1304 to deliver.

Although described above with respect to two devices, the illustrative technique of FIG. 13 may be extended to systems that include additional devices. For example, in such multiple device systems, a single device may send trigger signals 1306 to multiple devices of the system, causing multiple of the devices to deliver pacing pulses 1308 according to communicated or stored parameters and/or therapy protocols. In such examples, a first device may send such trigger signals at slightly different times to multiple different devices, thereby causing each of the receiving devices to deliver pacing pulses at slightly different times.

In some instances, a first device may send trigger signals to only one of the other multiple devices. For example, a first device may send trigger signals to the particular device that sensed a depolarization wave of the heart last relative to the other devices of the multiple device system. In still other examples, multiple devices may send trigger signals to multiple other devices, if desired. In some instances, the first device may be a subcutaneous cardioverter-defibrillators (S-ICD), and the other devices may be leadless cardiac pacemakers (LCPs), but this is just one example.

In some examples, a system may be capable of operating using some or all of the above described techniques in any combination. In such examples, each of the devices of the system may receive a communication signal indicating by which mode of operation the devices should operate. In some cases, each of the devices may have an address, and the communication between devices may be directed to particular devices by referencing the appropriate address(es). In some cases, the communication is simply broadcast to all devices, as desired.

Figure 14:
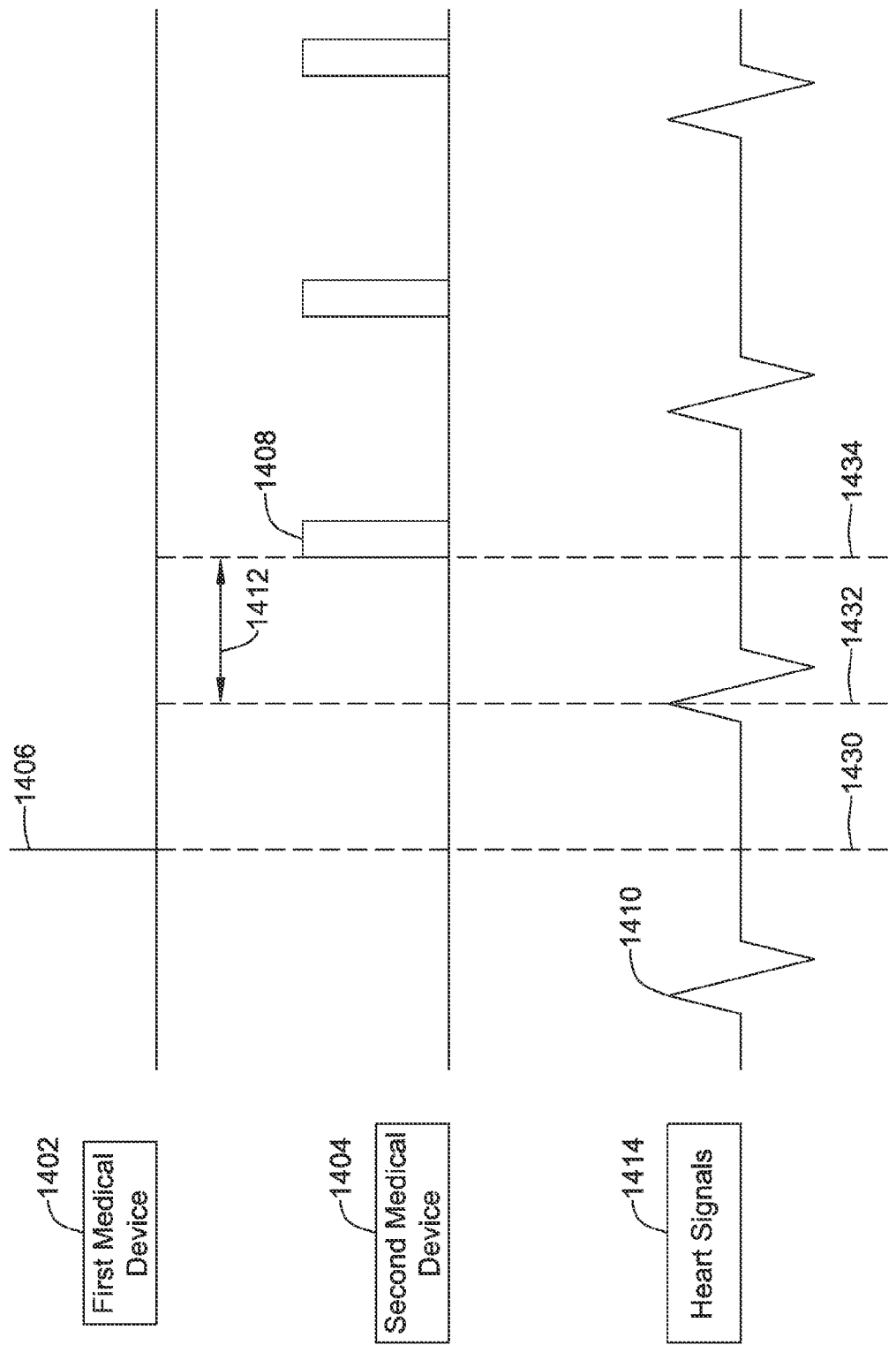
FIG. 14 shows an illustrative timing chart where a trigger signal from a first device cause a second device to deliver pacing pulses at particular times relative to sensed QRS waves of the heart.

FIG. 14 shows another illustrative technique by which at least two devices of a medical device system may coordinate to deliver electrical stimulation therapy. FIGS. 11-13 above described how multiple devices may coordinate to deliver electrical stimulation to a heart by communicating one or more trigger signals, with the trigger signals causing one or more medical devices to deliver electrical stimulation therapy to the heart. FIG. 14 illustrates particular timing considerations between when a device receives a trigger signal 1406 to deliver electrical stimulation therapy and when electrical stimulation therapy is actually delivered.

In the example shown in FIG. 14, a first medical device 1402 communicates a trigger signal 1406 to a second medical device 1404 when an arrhythmia is detected. In accordance with any of the techniques described above, after receiving the trigger signal 1406, the second medical device 1404 may deliver pacing pulses 1408 to the heart. In some cases, the second medical device 1404 may not deliver the pacing pulses 1408 immediately after receiving the trigger signal 1406, as shown in FIG. 14. For example, it may be beneficial for the second medical device 1404 to deliver pacing pulses during a particular period of the cardiac cycle of the heart.

Heart signals 1414 can be used to identify the cardiac cycles of the heart. In the example shown, the heart signals 1414 include QRS waves 1410, which in some cases can be sensed by the second medical device 1404. Generally, a heart is not able to contract in response to electrical stimulation just after a contraction of the heart (i.e. during a refectory period). After a certain time passes after a contraction, the cells of the heart may again be contracted in response to electrical stimulation. Accordingly, in order to deliver electrical stimulation therapy with a higher chance of causing a contraction of the heart or a high chance of terminating an arrhythmia, second medical device 1404 may wait to deliver pacing pulses until after the refractory period expires.

In the example shown in FIG. 14, the first medical device 1402 may communicate trigger signal 1406 after a first QRS wave 1410 and at a first time 1430. After receiving the trigger signal 1406, the second medical device 1404 may wait for a next QRS wave 1410. After sensing a QRS wave 1410 at second time 1432, the second medical device 1404 may wait a predefined time period 1412 before delivering pacing pulses 1408 at a third time 1434. Time period 1412 may be predefined such that when the second medical device 1404 delivers pacing pulses 1408, the second medical device 1404 delivers pacing pulses 1408 during a non-refractory period of the heart or at a time that has a greater likelihood of terminating an arrhythmia. Each subsequent delivered pacing pulse 1408 may be delivered during subsequent non-refractory periods. For example, a pacing pulse 1408 may be delivered a predefined time period 1412 following each subsequent QRS wave 1410. In some instances, predefined time period 1412 may be a parameter of pacing pulses 1408 that is communicated to the second medical device 1404 from, for example, the first medical device 1402, but this is not required.

In some examples, the second medical device, which delivers the electrical stimulation therapy to the heart, may synchronize delivering of the therapy with one or more defibrillation pulses. As one example, a medical system may include an LCP that is configured to deliver ATP therapy. The system may further include an SICD that is configured to deliver defibrillation pulses. After the system determines an occurrence of an arrhythmia, in accordance with any of the techniques described herein, the SICD may send a trigger signal to the LCP to deliver pacing pulses in accordance with an ATP therapy protocol, such as in accordance with any of the illustrative techniques described herein with respect to FIGS. 11-14. During the time that the LCP is delivering ATP therapy, the SICD may be charging a capacitor or the like to deliver a defibrillation pulse. Once the SICD has fully charged the capacitor or the like for the defibrillation pulse, the SICD may communicate with the LCP to stop delivering ATP therapy, for example by communicating a stop trigger signal or the like. In other examples, the LCP may be configured to deliver ATP for only a certain amount of time, for example in response to a stored or received pulse train length parameter, which may or may not coincide with the time it takes for the SICD to fully charge the capacitor. After the LCP ceases delivering ATP therapy, the system may confirm that the arrhythmia is still occurring. If the system determines that the arrhythmia is still occurring, the SICD may deliver a defibrillation pulse to the heart. If the system determines that no arrhythmia is still occurring, the system may return to a normal state of operation.

In some instances, the LCP device may be the trigger sending device, where the trigger to the SICD causes the SICD to begin charging for a defibrillation pulse. Another communication from the LCP may either cause the SICD to deliver the defibrillation pulse or abort delivering the defibrillation pulse, depending on whether an arrhythmia is still detected.

In some instances, the SICD determines whether an arrhythmia is occurring. The SICD may determine whether an arrhythmia is occurring by itself, or in conjunction with inputs received from one or more LCP or other devices. The SICD may then send a trigger signal to begin ATP therapy. After receiving the trigger signal, an LCP may verify a presence of an arrhythmia based on its own logic, before beginning to deliver ATP therapy. For example, the LCP may sense, or receive sensed cardiac electrical data, and from that data determine whether an arrhythmia is occurring.

In some cases, an LCP may operate in a normal state with an inactive communication link to an SICD. In such examples, the LCP may not receive or may block signals sent from the SICD, such as trigger signals. In such examples, the LCP may only activate the communication link after the LCP has itself determined an occurrence of an arrhythmia. In other examples the LCP may only activate the communication link after the LCP has itself determined the likelihood of an arrhythmia is high or the likelihood of an arrhythmia occurring in the near future (e.g. 1 to 60 minutes) is high. In such examples, keeping the communication link inactive may increase the battery life of the LCP.

Although some of the above examples have been described with respect to an LCP and an SICD, the disclosed method and techniques are applicable to any suitable system including the system disclosed herein, for example systems that include different types of devices and/or system that include different numbers of devices.

Figure 15:
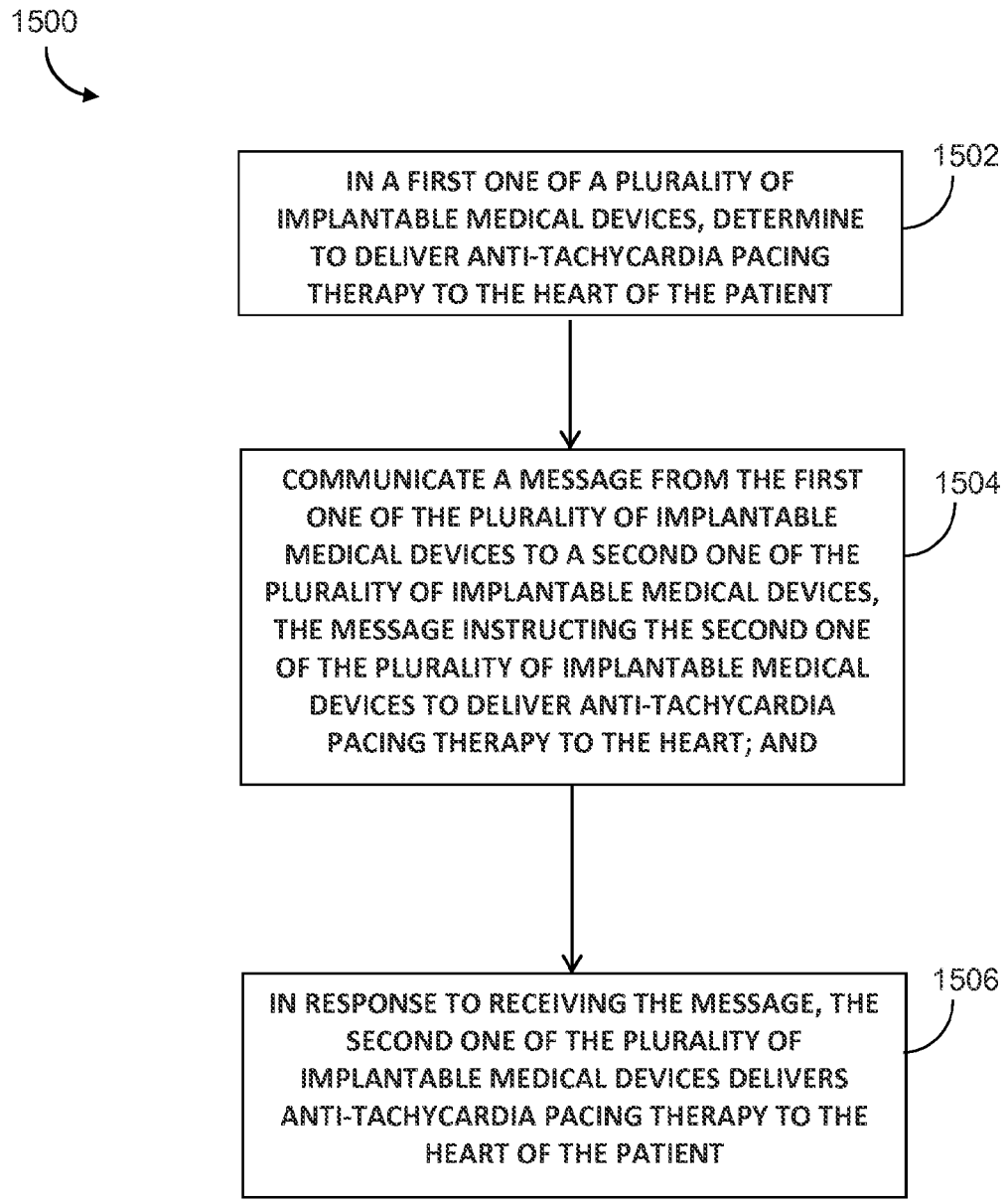
FIG. 15 is a flow diagram of an illustrative method that may be implemented by a medical device system, such as the illustrative medical device systems described with respect to FIGS. 3-10.

FIG. 15 is a flow diagram showing an illustrative method 1500 that can be implemented by an illustrative medical system. In FIG. 15, a first one of a plurality of implantable medical devices may determine to deliver anti-tachycardia pacing therapy to the heart of a patient, as shown at 1502. For example, one or more of the plurality of implantable medical devices may sense and/or receive cardiac data. Based on the sensed and/or received cardiac data, one or more of the plurality of implantable medical devices may determine an occurrence of an arrhythmia, such as in accordance with any of the techniques described herein. Subsequently, the first one of the plurality of implantable medical devices may communicate a message to a second one of the plurality of implantable medical devices. The message may instruct the second one of the plurality of implantable medical devices to deliver anti-tachycardia pacing (ATP) therapy to the heart, as shown at 1504. For example, the first one of the plurality of implantable medical devices may send a trigger signal to the second one of the plurality of implantable medical devices, such as in accordance with any of the techniques described herein. In response to receiving the message, the second one of the plurality of implantable medical devices may deliver anti-tachycardia pacing (ATP) therapy to the heart of the patient, as shown at 1506. For example, the second one of the plurality of implantable medical devices may deliver ATP therapy in response to receiving a trigger signal, such as in accordance with any of the techniques described herein.

Figure 16:
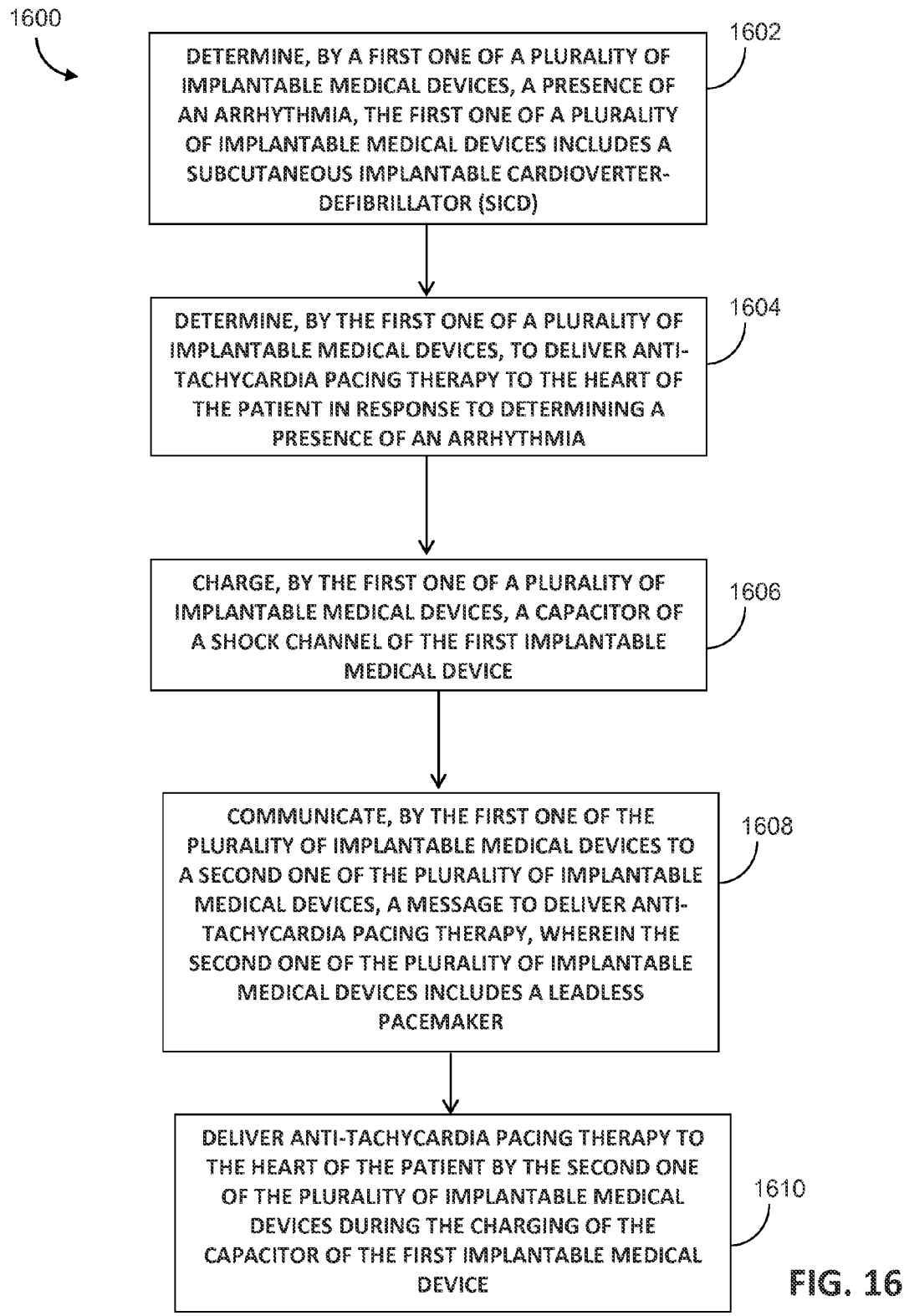
FIG. 16 is a flow diagram of an illustrative method that may be implemented by a medical device system, such as the illustrative medical device systems described with respect to FIGS. 3-10.

FIG. 16 is a flow diagram showing an illustrative method 1600 that can be implemented by an illustrative medical system. In FIG. 16, a first one of a plurality of implantable medical devices may determine a presence of an arrhythmia, where the first one of the plurality of implantable medical devices may include an SICD, as shown at 1602. In one example, the SICD may sense one or more cardiac signals, and/or receive one or more cardiac electrical signals from other devices. The SICD may, based on an analysis of the sensed and/or received cardiac signals, determine an occurrence of an arrhythmia. The first one of the plurality of implantable medical devices (e.g. SICD) may then determine to deliver anti-tachycardia pacing therapy to the heart of the patient in response to determining a presence of an arrhythmia, as shown at 1604. For example, the SICD may determine that the determined arrhythmia is a tachycardia and may further determine that is desirable for the system to deliver ATP therapy in response to the determined tachycardia. In some cases, the SICD may then begin to charge a capacitor of a shock channel in anticipation of delivering a defibrillation pulse in response to the determined tachycardia, as shown at 1606. In some instances, charging the capacitor may take a particular, non-instantaneous amount of time. The SICD may then communicate to a second one of the plurality of implantable medical devices a message to deliver anti-tachycardia pacing therapy to the heart, wherein the second one of the plurality of implantable medical devices may be a leadless pacemaker, as shown at 1608. For example, the SICD may send a trigger signal to an LCP, such as in accordance with any of the techniques described herein. The LCP may then deliver anti-tachycardia pacing (ATP) therapy to the heart during the charging of the capacitor of the SICD, as shown at 1610. In some instances, the LCP may coordinate delivering ATP therapy with the defibrillation pulse of the SICD, for example as described above with reference to FIG. 14.

Those skilled in the art will recognize that the present disclosure may be manifested in a variety of forms other than the specific embodiments described and contemplated herein. As one example, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure.

Additional Examples

In a first example, a method for delivering anti-tachycardia pacing therapy to a heart of a patient comprises, in a first one of a plurality of implantable medical devices, determining to deliver anti-tachycardia pacing therapy to the heart of the patient, communicating a message from the first one of the plurality of implantable medical devices to a second one of the plurality of implantable medical devices, the message instructing the second one of the plurality of implantable medical devices to deliver anti-tachycardia pacing therapy to the heart, and in response to receiving the message, the second one of the plurality of implantable medical devices delivering anti-tachycardia pacing therapy to the heart of the patient.

Alternatively, or in addition, and in a second example, the message of the first example may be a trigger.

Alternatively, or in addition, and in a third example, the first one of the plurality of implantable medical devices of any of the first or second examples may comprise a subcutaneous implantable cardioverter-defibrillator (SICD), and the second one of the plurality of implantable medical devices comprises a leadless pacemaker (LCP).

Alternatively, or in addition, and in a fourth example, delivering anti-tachycardia pacing therapy by the second one of the plurality of implantable medical devices of any of the first through third examples may comprise delivering a single electrical stimulation pulse by the second one of the plurality of implantable medical devices in response to the received message to deliver anti-tachycardia pacing therapy.

Alternatively, or in addition, and in a fifth example, delivering anti-tachycardia pacing therapy by the second one of the plurality of implantable medical devices of any of the first through fourth examples may comprise delivering multiple electrical stimulation pulses by the second one of the plurality of implantable medical devices in response to the received message to deliver anti-tachycardia pacing therapy.

Alternatively, or in addition, and in a sixth example, delivering anti-tachycardia pacing therapy by the second one of the plurality of implantable medical devices of any of the first through fifth examples may comprise delivering anti-tachycardia pacing therapy in accordance with an anti-tachycardia pacing therapy protocol.

Alternatively, or in addition, and in a seventh example, any of the first through sixth examples may further comprise communicating one or more anti-tachycardia pacing therapy parameters from the first one of a plurality of implantable medical devices to the second one of a plurality of implantable medical devices prior to the delivering step.

Alternatively, or in addition, and in an eighth example, the one or more anti-tachycardia pacing therapy parameters of the seventh example may include one or more of: a number of electrical stimulation pulses to deliver during delivery of anti-tachycardia pacing therapy; a width of electrical stimulation pulses to deliver during delivery of anti-tachycardia pacing therapy; an amplitude of electrical stimulation pulses to deliver during delivery of anti-tachycardia pacing therapy; a time period between electrical stimulation pulses to deliver during delivery of anti-tachycardia pacing therapy; a shape of electrical stimulation pulses to deliver during delivery of anti-tachycardia pacing therapy; a coupling interval; and a specific anti-tachycardia pacing therapy protocol.

Alternatively, or in addition, and in a ninth example, delivering anti-tachycardia pacing therapy by the second one of the plurality of implantable medical devices of any of the first through eighth examples may comprise beginning to deliver anti-tachycardia pacing therapy during a non-refractory period of the heart.

Alternatively, or in addition, and in a tenth example, delivering anti-tachycardia pacing therapy by the second one of the plurality of implantable medical devices of any of the first through ninth examples may comprise beginning to deliver anti-tachycardia pacing therapy after a predefined amount of time following a first QRS wave that is detected after receiving the message to deliver anti-tachycardia pacing therapy.

Alternatively, or in addition, and in an eleventh example, any of the first through tenth examples may comprise determining, by the second one of the plurality of implantable medical devices, a presence of an arrhythmia before delivering anti-tachycardia pacing therapy to the heart of the patient.

Alternatively, or in addition, and in a twelfth example, the second one of the plurality of implantable medical devices of any of the first through eleventh examples may deliver tachycardia pacing therapy to the heart of the patient in synchrony with the rhythm of the heart of the patient.

Alternatively, or in addition, and in a thirteenth example, a communication link of the second one of the plurality of implantable medical devices of any of the first through twelfth examples may be inactive until the second one of the plurality of implantable medical devices determines a presence of an arrhythmia or a predetermined heart rate.

Alternatively, or in addition, and in a fourteenth example, the communication by the first one of the plurality of implantable medical devices to the second one of the plurality of implantable medical devices of any of the first through thirteenth examples may be via conducted communication signals.

In a fifteenth example, an implantable medical device system for delivering anti-tachycardia pacing therapy to a heart of a patient comprises a first implantable medical device, a second implantable medical device, wherein the first implantable medical device and the second implantable medical device are communicatively coupled, wherein at least one of the first implantable medical device and the second implantable medical device is configured to deliver anti-tachycardia pacing therapy to the heart of the patient, wherein the first implantable medical device is configured to determine to deliver anti-tachycardia pacing therapy to the heart of the patient, wherein the first implantable medical device is configured to communicate a message to the second implantable medical device to deliver anti-tachycardia pacing therapy to the heart of the patient, and the second implantable medical device is configured to deliver anti-tachycardia pacing therapy to the heart in response to receiving the message.

Alternatively, or in addition, and in a sixteenth example, the message of the fifteenth example received by the second implantable medical device to deliver anti-tachycardia pacing therapy to the heart of the patient may cause the second implantable medical device to deliver one anti-tachycardia pacing pulse, and wherein the first implantable medical device is configured to communicate multiple messages to the second implantable medical device wherein each message causes the second implantable medical device to deliver a corresponding anti-tachycardia pacing pulse.

Alternatively, or in addition, and in a seventeenth example, the first implantable medical device of any of the fifteenth or sixteenth examples may be further configured to communicate one or more parameters of the anti-tachycardia pacing therapy to the second implantable medical device.

Alternatively, or in addition, and in an eighteenth example, the first implantable medical device of any of the fifteenth-seventeenth examples may comprise a subcutaneous implantable cardioverter-defibrillator (SICD), and the second implantable medical device comprises a leadless pacemaker (LCP).

In a nineteenth example, a method of delivering electrical stimulation therapy to a heart of a patient comprises determining, by a first one of a plurality of implantable medical devices, a presence of an arrhythmia, the first one of a plurality of implantable medical devices includes a subcutaneous implantable cardioverter-defibrillator (SICD), determining, by the first one of the plurality of implantable medical devices, to deliver anti-tachycardia pacing therapy to the heart of the patient in response to determining a presence of an arrhythmia, charging, by the first one of the plurality of implantable medical devices, a capacitor of a shock channel of the first one of the plurality of implantable medical device, communicating, by the first one of the plurality of implantable medical devices to a second one of the plurality of implantable medical devices, a message to deliver anti-tachycardia pacing therapy, wherein the second one of the plurality of implantable medical devices includes a leadless pacemaker, and delivering anti-tachycardia pacing therapy to the heart of the patient by the second one of the plurality of implantable medical devices during the charging of the capacitor of the first one of the plurality of implantable medical devices.

Alternatively, or in addition, and in a twentieth example, the first one of the plurality of implantable medical devices of the nineteenth example may be configured to determine a presence of an arrhythmia or a predetermined heart rate after the second one of the plurality of implantable medical devices begins to deliver anti-tachycardia pacing therapy to the heart of the patient, and if the first one of the plurality of implantable medical devices determines a presence of an arrhythmia or a predetermined heart rate, the first one of the plurality of implantable medical devices is configured to deliver a defibrillation pulse to the heart of the patient via the shock channel.

What is claimed is:

1. A method for delivering anti-tachycardia pacing therapy to a heart of a patient, the method comprising:
   in a first one of a plurality of implantable medical devices, determining to deliver anti-tachycardia pacing therapy to the heart of the patient;
   communicating a message from the first one of the plurality of implantable medical devices to a second one of the plurality of implantable medical devices, the message instructing the second one of the plurality of implantable medical devices to deliver anti-tachycardia pacing therapy to the heart, the message including one or more anti-tachycardia pacing therapy parameters provided by the first one of a plurality of implantable medical devices; and in response to receiving the message that includes the one or more anti-tachycardia pacing parameters and the instruction to deliver anti-tachycardia pacing therapy to the heart, the second one of the plurality of implantable medical devices delivering a first one of a plurality of electrical stimulation pulses to the heart of the patient after a predefined amount of time following a QRS wave that is detected by the second one of the plurality of implantable medical devices after receiving the message, wherein the plurality of electrical stimulation pulses are based on the one or more anti-tachycardia pacing parameters that were included in the message.

2. The method of claim 1, wherein the message is a trigger for delivery of the plurality of electrical stimulation pulses.

3. The method of claim 1, wherein the first one of the plurality of implantable medical devices comprises a subcutaneous implantable cardioverter-defibrillator (SICD), and the second one of the plurality of implantable medical devices comprises a leadless pacemaker (LCP).

4. The method of claim 1, further comprising delivering anti-tachycardia pacing therapy in accordance with an anti-tachycardia pacing therapy protocol.

5. The method of claim 1, wherein the one or more anti-tachycardia pacing therapy parameters provided by the first one of the plurality of implantable medical devices include one or more of: a pulse width of the plurality of electrical stimulation pulses; an amplitude of the plurality of electrical stimulation pulses and a shape of the plurality of electrical stimulation pulses.

6. The method of claim 1, further comprising beginning to deliver the plurality of electrical stimulation pulses during a non-refractory period of the heart.

7. The method of claim 1, further comprising determining, by the second one of the plurality of implantable medical devices, a presence of an arrhythmia before delivering the plurality of electrical stimulation pulses.

8. The method of claim 1, wherein the second one of the plurality of implantable medical devices delivers the plurality of electrical stimulation pulses in synchrony with the rhythm of the heart of the patient.

9. The method of claim 1, wherein a communication link of the second one of the plurality of implantable medical devices is inactive until the second one of the plurality of implantable medical devices determines a presence of an arrhythmia or a predetermined heart rate.

10. The method of claim 1, wherein the communication by the first one of the plurality of implantable medical devices to the second one of the plurality of implantable medical devices is via conducted communication signals.

11. An implantable medical device system for delivering anti-tachycardia pacing therapy to a heart of a patient, the system comprising:

a first implantable medical device;
a second implantable medical device, wherein the first implantable medical device and the second implantable medical device are communicatively coupled;
wherein at least one of the first implantable medical device and the second implantable medical device is configured to deliver anti-tachycardia pacing therapy to the heart of the patient;
wherein the first implantable medical device is configured to determine to deliver anti-tachycardia pacing therapy to the heart of the patient;
wherein the first implantable medical device is configured to communicate multiple messages to the second implantable medical device to deliver anti-tachycardia pacing therapy to the heart of the patient; and
the second implantable medical device is configured to deliver one anti-tachycardia pacing pulse to the heart in response to receiving each of the multiple messages.

12. The system of claim 11, wherein the first implantable medical device is further configured to communicate one or more parameters of the anti-tachycardia pacing therapy to the second implantable medical device.

13. The system of claim 11, wherein the first implantable medical device comprises a subcutaneous implantable cardioverter-defibrillator (SICD), and the second implantable medical device comprises a leadless pacemaker (LCP).

14. A method for delivering anti-tachycardia pacing therapy to a heart of a patient, the method comprising:
in a first one of a plurality of implantable medical devices, determining to deliver anti-tachycardia pacing therapy to the heart of the patient;
communicating a message from the first one of the plurality of implantable medical devices to a second one of the plurality of implantable medical devices, the message instructing the second one of the plurality of implantable medical devices to deliver anti-tachycardia pacing therapy to the heart; and
in response to receiving the message, the second one of the plurality of implantable medical devices delivering anti-tachycardia pacing therapy to the heart of the patient, the second one of the plurality of implantable medical devices configured to begin delivering anti-tachycardia pacing therapy after a predefined amount of time following a QRS wave that is detected by the second one of the plurality of implantable medical devices after receiving the message to deliver anti-tachycardia pacing therapy.

15. The method of claim 14, wherein the second one of the plurality of implantable medical devices is configured to begin delivering anti-tachycardia pacing therapy during a non-refractory period of the heart.

* * * * *